United States Patent
Alemi et al.

(10) Patent No.: US 11,825,377 B2
(45) Date of Patent: Nov. 21, 2023

(54) USING WI-FI INFRASTRUCTURE TO PREDICT LOCATIONS AND CONTACTS

(71) Applicant: George Mason University, Fairfax, VA (US)

(72) Inventors: Farrokh Alemi, Fairfax, VA (US); Janusz Wojtusiak, Fairfax, VA (US)

(73) Assignee: GEORGE MASON RESEARCH FOUNDATION, INC. OF FAIRFAX VIRGINIA, Fairfax, VA (US)

( * ) Notice: Subject to any disclaimer, the term of this patent is extended or adjusted under 35 U.S.C. 154(b) by 226 days.

(21) Appl. No.: 17/495,340

(22) Filed: Oct. 6, 2021

(65) Prior Publication Data
US 2022/0109949 A1    Apr. 7, 2022

Related U.S. Application Data

(60) Provisional application No. 63/088,145, filed on Oct. 6, 2020.

(51) Int. Cl.
| | | |
|---|---|---|
| H04W 24/00 | (2009.01) | |
| H04W 4/02 | (2018.01) | |
| A61B 5/00 | (2006.01) | |
| H04W 4/029 | (2018.01) | |
| H04W 84/12 | (2009.01) | |

(52) U.S. Cl.
CPC .......... *H04W 4/023* (2013.01); *A61B 5/7275* (2013.01); *H04W 4/025* (2013.01); *H04W 4/029* (2018.02); *H04W 84/12* (2013.01)

(58) Field of Classification Search
CPC ..... H04W 4/023; H04W 4/029; A61B 5/7275
See application file for complete search history.

(56) References Cited

U.S. PATENT DOCUMENTS

2021/0391072 A1* 12/2021 Ergen ..................... G16H 50/80

FOREIGN PATENT DOCUMENTS

WO    WO-2022081315 A2 *    4/2022

* cited by examiner

Primary Examiner — Erika A Washington
(74) Attorney, Agent, or Firm — WCF IP

(57) ABSTRACT

Exemplary methods predict the locations of individuals in buildings over time based on Wi-Fi access point connectivity and other reference information. Predicted locations are used to predict risk of contact, for example of infected persons with others in public spaces.

18 Claims, 12 Drawing Sheets

USING WI-FI INFRASTRUCTURE TO PREDICT LOCATIONS AND CONTACTS

CROSS-REFERENCE TO RELATED APPLICATIONS

This application claims the benefit of U.S. provisional patent application No. 63/088,145, filed Oct. 6, 2020, the complete contents of which are hereby incorporated by reference.

FIELD OF THE INVENTION

The invention generally relates to predicting locations and movements using Wi-Fi access data and other types of information, and in particular, to contact tracing to improve public health outcomes.

BACKGROUND

Contact tracing can reduce transmission if exposed individuals are identified as soon as possible following contact with an infected person. The faster and more thorough contact tracing is, the smaller the number of people infected. Rapid contact tracing is an integral part of any strategy to contain epidemics. Unfortunately, contact tracing in the COVID-19 context has been hampered by a reliance on traditional, labor, and time intensive methods. Coupled with the sheer volume of cases and the high transmissibility of the virus, the collaboration between large organizations and public health agencies is necessary to respond to COVID-19 effectively. Large organizations like universities need to make efforts and complete in-house contact tracing. Because of the above reasons, COVID-19 has highlighted the need to develop and implement more rapid and innovative contact tracing protocols that integrate new technologies. Private and public employers alike are still looking for rapid and cost-effective solutions to contact tracing.

Technological support for contact tracing has been the focus of significant work within the past years and more intensely since the COVID-19 pandemic started.

Bluetooth beacon, Bluetooth Low Energy (BLE), and Wi-Fi are the most used technologies in indoor positioning and contact tracing. They are automated and faster than personal contact tracing. These methods keep the identity of an infected person confidential and only alert exposed individuals. They work on phones that have Wi-Fi and Bluetooth connectivity. Compared to a Wi-Fi-based system, Bluetooth is cheap and can be easily deployed. Bluetooth can also make up for the blind area of indoor Wi-Fi signal and realize the full coverage of indoor wireless signal. However, there has been widespread criticism of Bluetooth-based contact tracing systems primarily because of the requirement of extra hardware deployment instead of using existing Wi-Fi infrastructure. Another issue is some solutions, such as a 2020 Google/Apple Proposal (GAP), is vulnerability to profiling and possibly de-anonymization of infected persons, as well as relay-based wormhole attacks that can basically generate fake contacts with the potential of affecting the accuracy of an app-based contact tracing system.

When evaluating a positioning technology, the accuracy of positioning is one of the essential indicators to measure different indoor positioning techniques' performance. However, in many cases, other indicators such as cost, real-time performance, and reliability need to be considered. Excessive precision will only increase its cost and reduce its real-time performance, leading to a decrease in the quality of overall system evaluation. A commonly used form for Wi-Fi base positioning is that each user needs to actively carry a mobile device to search and collect nearby access point (AP) signals. The valid information from the signals of APs can be obtained, and then the data is transmitted to a server for processing. A less commonly used form is that each user does not need to carry any equipment, but a signal transmitter and signal receiver must be deployed. Considering the deployment cost and the popularization rate of smartphones in the population, the former approach requiring mobile devices on users is reasonable.

Some existing systems rely on the availability of RSSI information to run triangulation of multiple APs or Wi-Fi fingerprint to estimate a device's proximity. However, this adds difficulty in AP deployment and pre-signal-scanning. It also requires either access to RSSI data from each AP or specialized applications to be installed on smartphones; neither may be feasible in practice, especially during a COVID-19 pandemic or the like.

An alternative approach is based on the analysis of device association and disassociation time, which limits the privacy concern of relying on RSSI data and minimizes the deployment cost. The approach does not rely on any additional equipment or the need to install specialized apps on smartphones. Yet, there has not been much research on this approach.

One simple Wi-Fi based approach (referred to as the "N1" approach later in this disclosure) that can be used to list individuals that were potentially in contact is to check Wi-Fi connection logs for people connected to the same access point at the same time. The advantage of this method is that there is no need for any information about the location of access points, floorplans, or network structure. The approach simply calculates an intersection between connection logs of individuals. It is fast and can be readily deployed without any additional information about floorplans or AP locations. The disadvantage of this method is a possible low recall (sensitivity) in identifying potential contacts. Most locations within a building are covered by more than one access point, sometimes on different floors. And a single APs signal may reach multiple rooms at once. Recall and precision of this approach of predicting actual locations is significantly affected by the number of rooms covered by one access point and multiple access points covering one room.

Another simple Wi-Fi based approach (referred to as the "N2" approach later in this disclosure) is to simply list people who were in the same building at the same time. The only information about Wi-Fi access points needed is the building in which they are located. The method has very high recall (essentially 100% of people who connect to Wi-Fi, which is a very high percentage of all people in the building). The disadvantage of this approach is that it is impractical for use for contact tracing—potentially hundreds of individuals are in a building simultaneously but never interact or are present in the same room at the same time.

SUMMARY

To address deficiencies of existing methods such as methods N1 and N2 described above, exemplary processes of this disclosure first predict a set of likely locations in which individuals were physically present (with their associated probabilities) and then use the predicted locations to check which plural persons were likely to have been at the same place at the same time (with the inference they were therefore "in contact"). More specifically, exemplary embodiments maximize the precision (or specificity) of models to reduce the number of potential contacts returned by the method while maintaining recall as high as possible. A series of alternative approaches are described below that use increasingly sophisticated methods depending on the amount of information on which the decision making is based.

The exemplary processes herein provide tools that large organizations can employ to aid effective contact tracing, helping identify individuals that need to be contacted for follow up by personnel conducting contact tracing.

Contact tracing is a well-defined term in epidemiology and public health. It generally has the following steps: contact identification (contact elicitation), notification, monitoring, and follow up. According to the most rudimentary implementations, contact identification is typically performed by an infected patient during an interview process and therefore is entirely dependent on human observation, human memory, and human recall. The presented embodiments herein focus on contact prediction procedures that identify those who were in contact with an infected individual without a need to rely on human observation, human memory, or human recall (though actual human surveys and responses may still be incorporated in some embodiments). Accordingly these sources of human error are reduced substantially or else eliminated outright. The term contact prediction stresses the fact that contacts are identified (predicted) through computational methods. Results are especially suitable for use as part of contact tracing protocols by a variety of different types of institutions (e.g., universities, schools, school districts, corporate offices, businesses, law enforcement, correctional, government offices, etc.).

An exemplary process relies on the use of Wi-Fi network connection logs that are routinely collected by network infrastructure in enterprise environments such as university campuses and corporations. Neither Bluetooth data nor wireless carrier data is necessary or indeed used in some exemplary embodiments. The Wi-Fi data used may be generated using, for example, SNMP (Simple Network Management Protocol) traps. This is one exemplary means of collecting Wi-Fi data which requires no need to make any modifications to the network which may be costly and time consuming. Rather, the process requires only extraction of the connection logs from one or more networks and securely transmitting them to one or more computers (e.g., servers) for analysis. The information included in a log file may include timestamps of users' association and disassociation (i.e., connection and disconnection) with an access point (AP). Received signal strength indicator (RSSI) information is not required and typically not included in logs, but it may be collected in some instances as well.

The Detailed Description below and following Examples present three advantageous approaches to modeling Wi-Fi data, location prediction based on Wi-Fi data, as well as contact prediction methodology. The location prediction techniques are superior to prior approaches such as N1 and N2 discussed in the Background section.

Three exemplary approaches/methods for location prediction (referred to as P1, P2, and P3 respectively) are presented. Collectively they may be summarized together as follows. A first step is extracting Wi-Fi access point (AP) information for a plurality of mobile devices, each of the plurality of mobile devices being associated with a different individual of a plurality of people, the Wi-Fi access point information containing, for each mobile device, a list of one or more APs used for connecting to a network, one or more connection times of when the respective mobile device connected to each of the one or more APs, and one or more disconnection times of when the respective mobile device disconnected from each of the one or more APs. Then, for each AP connection of each mobile device, the next step is assigning a non-zero probability to any locations from which signal of the AP permits a connection and a zero probability to remaining locations. Finally, for each of one or more times or time intervals for each respective person of one or more of the people, the method requires determining a contact score between a first mobile device of the respective person and a second mobile device of a target person using the assigned probability for a first location for the first mobile device and the assigned probability for the first location for the second mobile device. If the two devices and thus the two persons only overlap in time in a single room, only that single room need be considered. Else, the contact score may be a sum of the contact probabilities for all the locations in which the two persons overlapped in time, as portrayed by the timing of connection and disconnection with APs.

The data for the Examples at the end of the Detailed Description employed real connection logs for participants accessing Wi-Fi networks at a university campus. More specifically, identifiable data from consenting individuals were collected and cross-checked with the individual's self-reported real locations and time at those locations. Using the collected real movement data of the 12 participants, the Examples shows that the approaches that rely on location prediction (referred to as P1, P2, and P3 respectively) are superior to more rudimentary Wi-Fi-based approaches to location tracing. Further, the Examples illustrate multiple simulated contact scenarios that validate the described location and contact tracing approaches in combination.

Exemplary methods herein may provide information for a decision support system in which a person conducting a case interview with an infected individual can have access to data about predicted locations and interactively confirm or disconfirm known locations, and add more places in which the infected person has been. The system may then produce a ranked list of potential contacts, each with an associated score, predicted location and predicted time of contact. Such information can then be used to conduct a more informed and thorough follow up with individuals as part of contact tracing protocol.

Once lists of likely locations are created for all people who were in a building at a given time, these lists can be intersected to calculate chances and time of contact between individuals. Consequently, if a person tests positive for COVID-19 or any other highly contagious disease, an accurate list of people with a potential contact to the infected individual is readily created.

While pandemic and public health applications are exemplary contexts of use for this technology, other applications may occur to those of skill in the art in view of this disclosure. For instance, law enforcement or government agencies may use the location and/or contact prediction approaches herein or variations thereon to identify and monitor public safety threats, criminal activity, collusion, or conspiracy.

DETAILED DESCRIPTION

Figure 1:
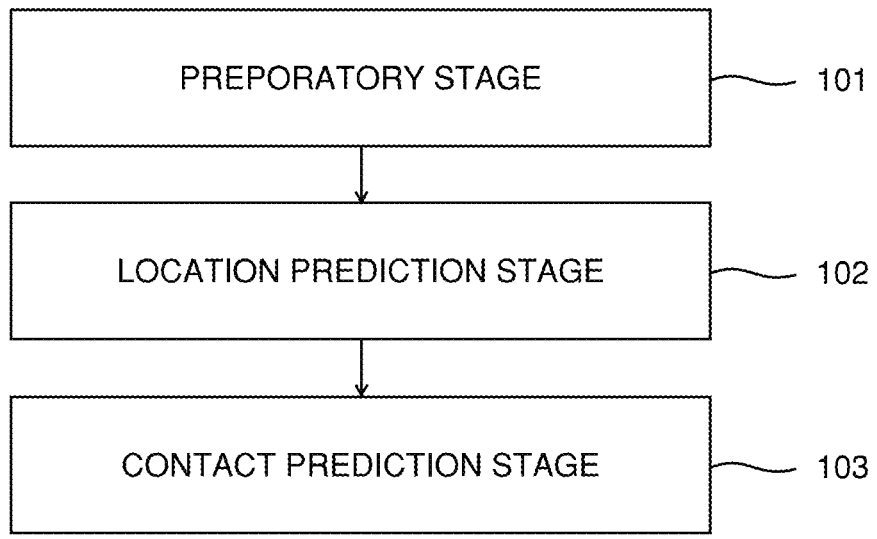
FIG. 1 is a flowchart of primary stages of an exemplary embodiment for location prediction and contact tracing.

FIG. 1 is an overview of primary stages of some exemplary embodiments. The contact prediction stage 103 is the final stage and provides predictions of contacts among a plurality of people. Prior to contact prediction, however, is a location prediction stage 102 which provides information on the locations, and in particular the series of locations forming a movement path, visited by respective ones of the people in question. Information concerning available locations that people may visit and the relationships among these locations is necessary, however, and may be generated in an initial preparatory stage 101. Altogether, prediction of likely contacts that can be used for contact tracing may require preparatory steps followed by the application of algorithms that estimate likely locations and then likely contacts. Likelihoods may be assessed using metrics such as probabilities.

Figure 2:
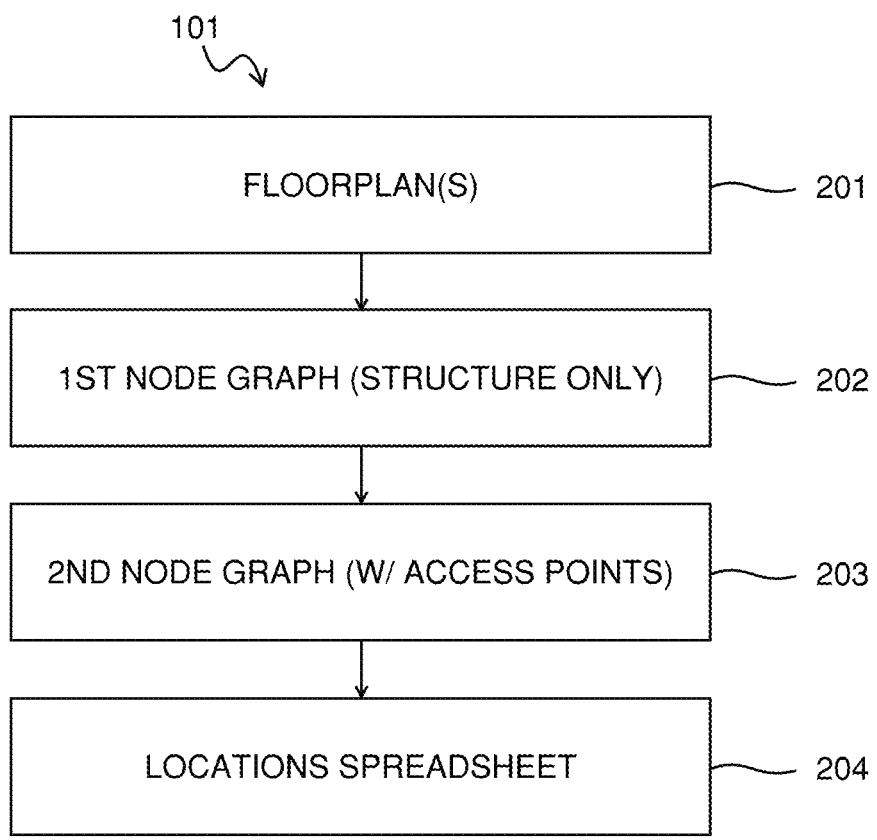
FIG. 2 is a flowchart of an exemplary method for preparing floorplans for digital use.

FIG. 2 presents an exemplary process for the preparatory stage 101 of FIG. 1. The role of preparatory stage 101 is to produce computer-interpretable representations of floorplans and Wi-Fi network infrastructure. The final form of this information is processible by semiautomated or fully automated location and contact prediction methods. The requisite modeling of FIG. 2 is possible provided a pre-existing Wi-Fi network with fixed access points (AP) and available building floorplans 201. In many actual implementations of the technology disclosed herein, available floorplans for public buildings will not be machine readable. They may be computer graphics, stored as jpg or tiff files for instance, or else pdf or pdf-like file types. The number of rooms shown, the size of the rooms, the relative arrangement of the rooms and paths between them, are at the time of writing this disclosure not often interpretable without a human. Of course, if such information is already available in a digitized and computer readable form, then the preparatory stage 101 may not be necessary.

A first step of process 101 comprises obtaining what floorplans 201 are available and extracting details such as room location, size, and capacity. Extraction may be accomplished manually, that is to say by human assessment, to produce a first node graph 202.

Figure 3A:
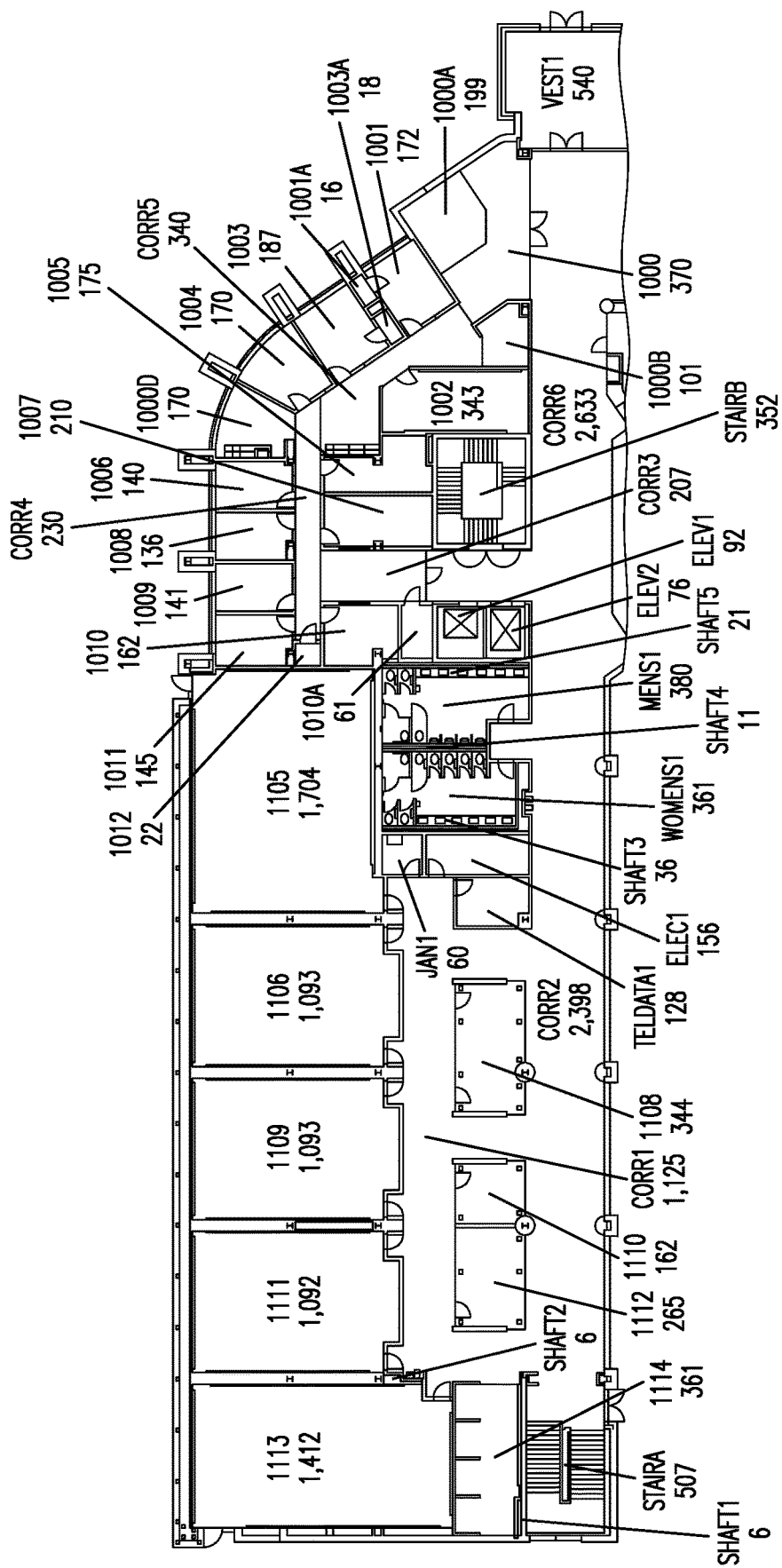
FIG. 3A is a sample floorplan.

FIG. 3A presents a sample floorplan of a public building. Owing to practical space limits, only a wing of a single large building is depicted. The floorplan is cutoff at the bottom right of the figure. Each room is designated with a number ID, with a square footage given below the number ID. The different types of spaces have labels consistent with industry norms that will be recognized by those of skill in the art. For instance, corridors are labeled "CORR . . . ", bathrooms "WOMENS . . . " or "MENS . . . ", stairs "STAIR . . . ", and elevators "ELEV . . . ".

Figure 3B:
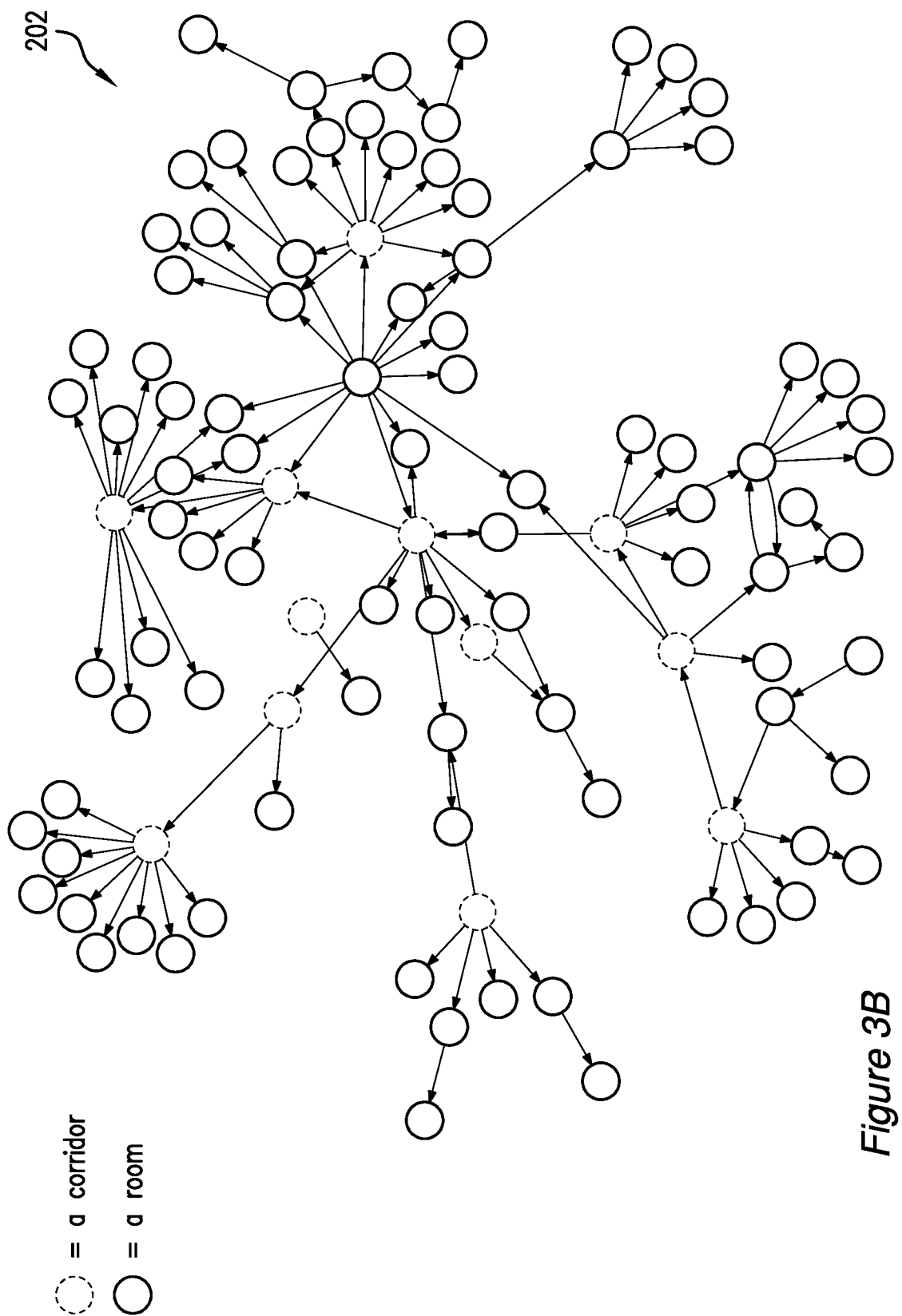
FIG. 3B is a node graph for the floorplan in FIG. 3A.

FIG. 3B presents a node graph 202 of the same floorplan. In the node graph 202, individual rooms and corridors are represented by individual nodes, and doorways, cased openings, entrances, exits, or other openings that allow movement from one room or corridor to another room or corridor are represented by edges between nodes. The node graph 202 resolves a floorplan purely into nodes and edges. The nodes are shaded or color coded to assist in reading, with one shade used for corridors and another used for all other types of spaces. In this disclosure, the term "locations" encompasses all the different types of physical spaces in which humans ordinarily fit. The term "room" is also used broadly in this disclosure and may encompass corridors, elevators, stairwells, bathrooms, and other spaces.

As mentioned above, because of page size limits, an entirety of the floorplan of the actual building represented in FIG. 3A could not be shown in FIG. 3A. FIG. 3B is more comprehensive of the actual building modeled for illustration, and therefore the node graph 202 contains a greater number of room/corridor nodes than the total number of rooms/corridors that would fit on the page for FIG. 3A.

Figure 3C:
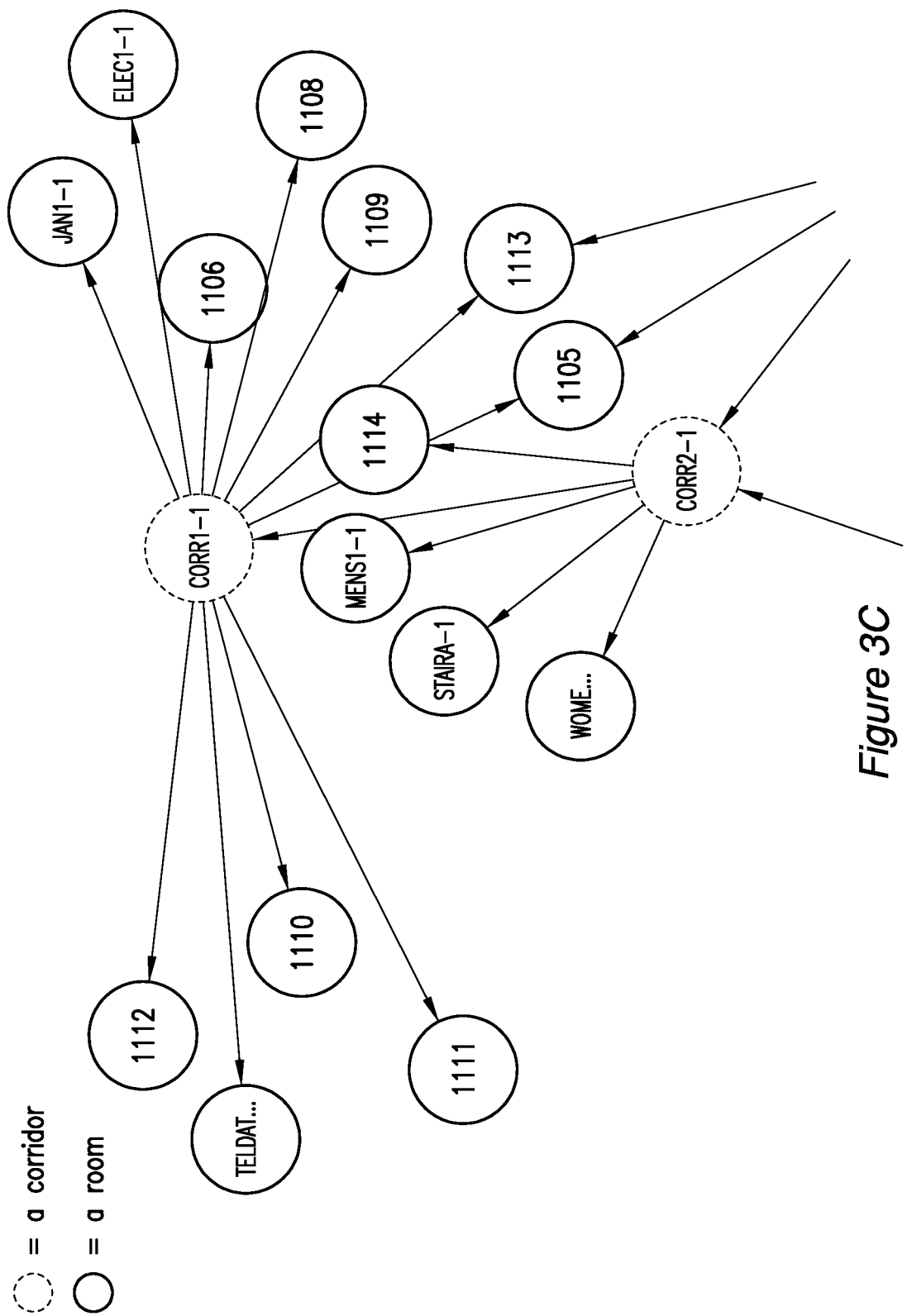
FIG. 3C is an enlargement of a section of the node graph from FIG. 3B.

FIG. 3C provides an enlargement of one section of the node graph 202 that corresponds with rooms at the far left of FIG. 3A. This enlargement serves merely to allow easier reading of labels for comparison of the node graph and floor plan for illustration purposes.

The nodes collectively identify all possible locations of people, including but not limited to rooms, corridors, bathrooms, elevators, stairwells, lobbies, offices, communal workspaces, halls (e.g., lecture halls), garages, and the like. For convenience of discussion, all such types of spaces in buildings may be collective referred to as "rooms" in this disclosure. The edges connect nodes to one another. A chain of nodes and edges, with a minimum of two nodes and one edge, constitutes a possible movement path of a person through the building floorplan. Despite the typical one dimensionality of floor plans, the node graph 202 advantageously takes into account the multidimensionality of buildings. An elevator node, for example, is able to share an edge with the hall or room node of each floor of the building with which the elevator reaches. Similarly, a stairwell node will have edges to every hall or room with which the stairwell has a door or opening. Thus all the floorplans for a single building, or even a single campus "(e.g., college, trade school, K-12 school; indoor or outdoor shopping mall; hospital or clinic; elder care facility; prison, etc.), may be represented together in a single node graph 202 if desired.

FIG. 2's next step is using the first node graph 202, together with Wi-Fi network infrastructure information, to produce a second node graph 203. The second node graph 203 differs from the first node graph 202 in that, in addition to representing locations (as location nodes) and their physical connections (as edges), the second node graph 203 includes a second type of node that reflects the relationship of access points (APs) with the room locations. Each AP is represented as a single node. A single AP with signal reaching three rooms is, for example, represented as a single AP node with three edges, one to connect the AP node with each the three respective room nodes where the AP's signal strength is sufficient to connect to the Wi-Fi network.

Figure 3D:
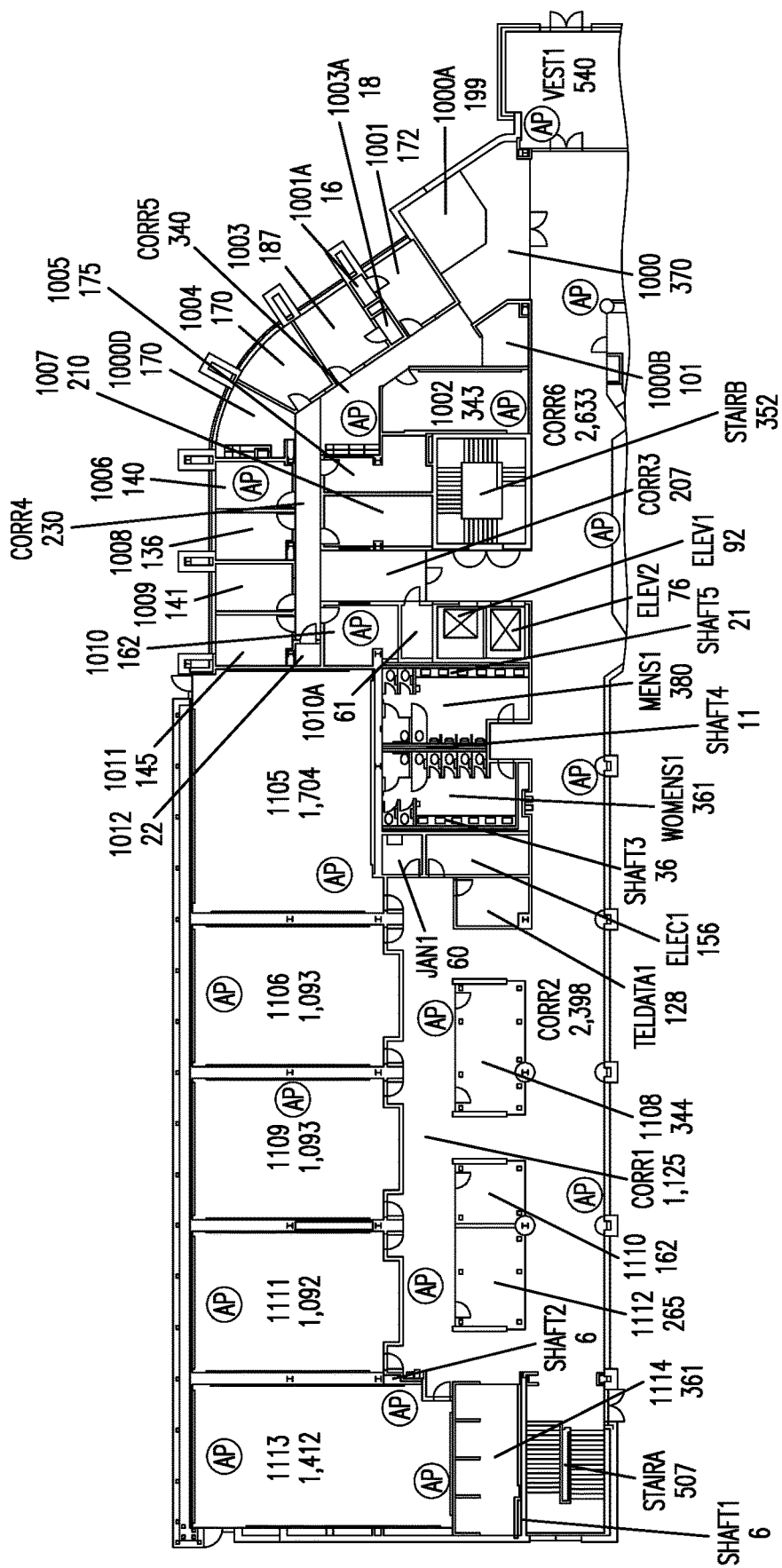
FIG. 3D is a map of Wi-Fi access point (AP) placement for the floorplan of FIG. 3A.

FIG. 3D provides a visual representation of access point locations with respect to the rooms in the sample floorplan of FIG. 3A. Each AP is represented by "AP" in a circle at its physical location in the building represented by the floorplan.

Figure 3E:
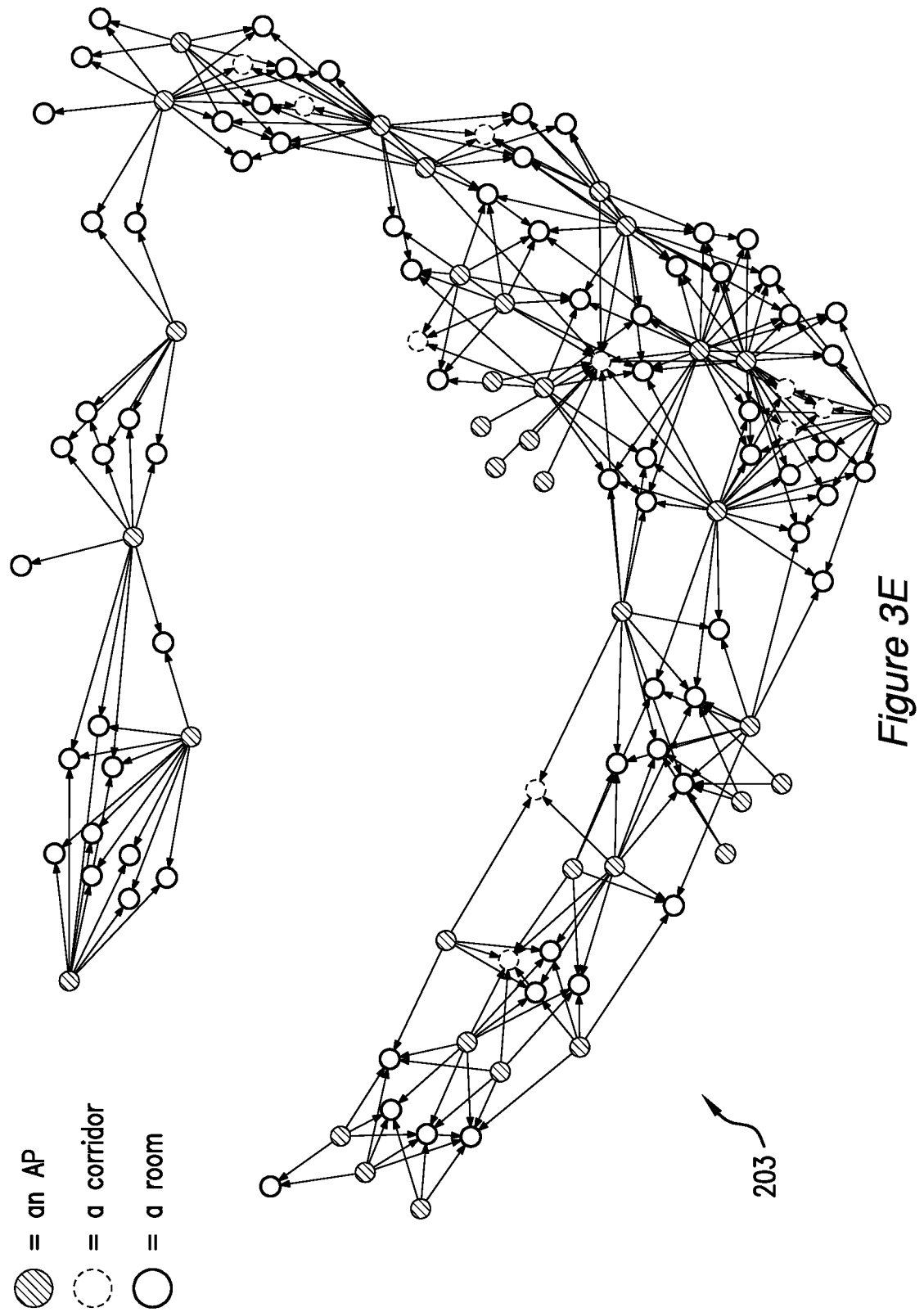
FIG. 3E is a second node graph that reflects both the floorplan of FIG. 3A and the Wi-Fi AP layout of FIG. 3D.

FIG. 3E shows the complete second node graph 203 based on first node graph 202 but modified to reflect the locations of APs from FIG. 3D. The nodes are shaded or color coded to assist in reading, with one shade used for corridors, a second shade used for rooms, and a third shade used for APs. The number of AP nodes matches the number of APs with which devices in the building are permitted to connect. However, as mentioned above, because of page size limits, an entirety of the floorplan of the actual building represented in FIG. 3A could not be shown in FIGS. 3A and 3D. FIG. 3E is more comprehensive of the actual building modeled for illustration, and therefore the node graph 203 contains a greater number of both AP nodes and room/corridor nodes than the total number of APs and rooms/corridors that would fit on the pages for FIGS. 3A and 3D. The edges connecting AP nodes with room nodes may additionally carry signal strength information (e.g., RSSI).

Figure 3F:
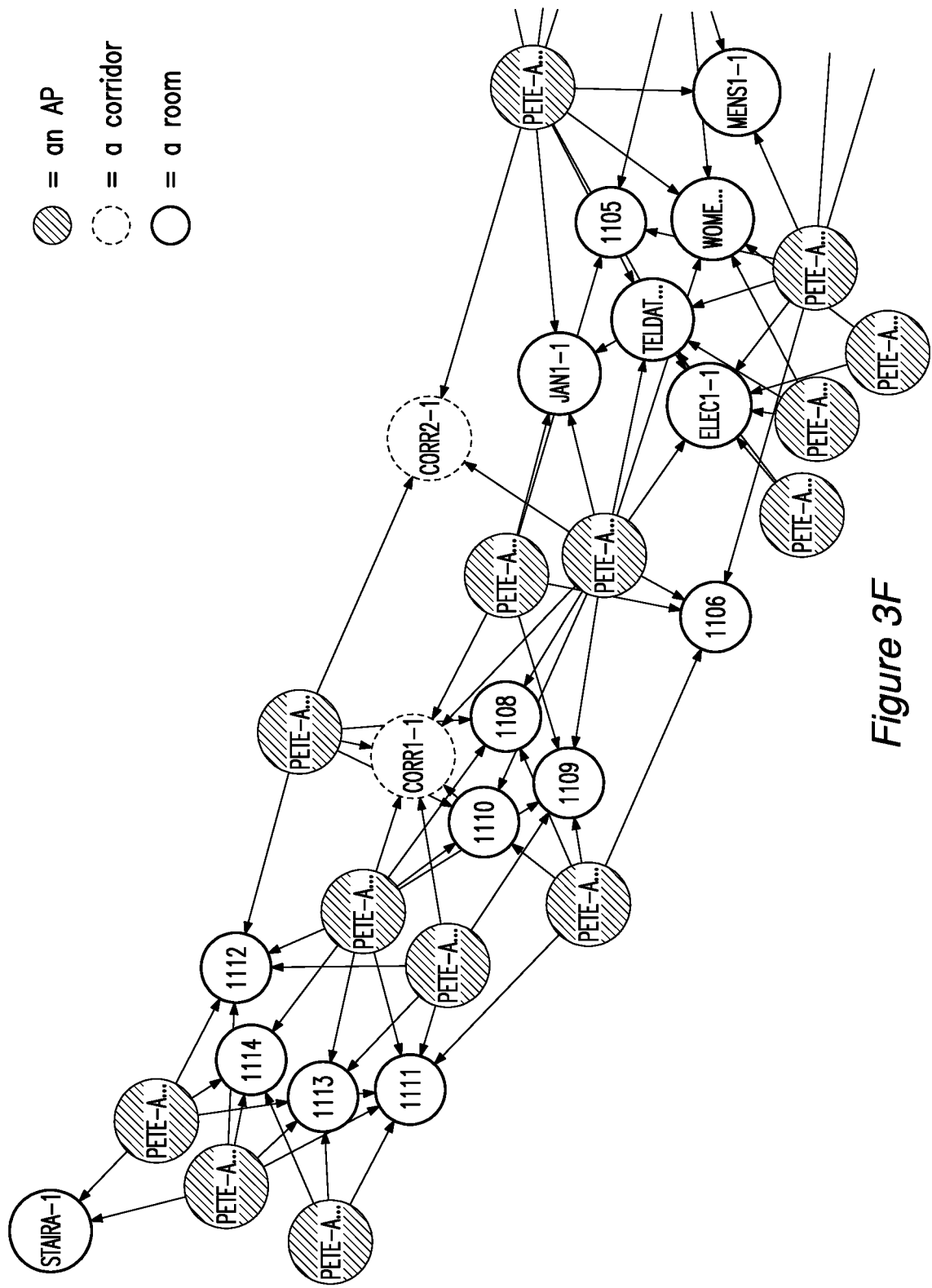
FIG. 3F is an enlargement of a section of the node graph from FIG. 3E.

FIG. 3F provides an enlargement of one section of the node graph 203 that corresponds with rooms and APs at the far left of FIG. 3A. This enlargement serves merely to allow easier reading of labels for comparison of the node graph and floor plan for illustration purposes. Note also that, as is typical for node graphs, the node graph visualization does not necessarily spatially align with the floorplan visualization. For instance, the rooms at the far left of the floorplan are represented by nodes that are not necessarily at the far left of the node graph.

Node graph architecture as just described above is one exemplary software design technique for modeling the floorplan and building infrastructure in a manner understandable to and usable by computers. The node graph may be used to yield a list 204 of all possible rooms/locations any person within a building (or buildings) may visit, which in turn is usable to produce a list of locations in which any given person was likely to be during a given period of time. The list of possible locations may be stored in a spreadsheet or other acceptable data storage format.

Returning to FIG. 1, the location prediction stage 102 of exemplary embodiments generally comprises predicting the location at any given time, or multiple locations over a time period/duration, of individuals in the building or on the campus for which the node graph and available locations list were prepared in the preparatory stage 101. Following are three alternative exemplary approaches to location prediction, labeled respectively P1, P2, and P3 for ease of discussion and comparison in the Examples section that follows.

For contact tracing, such as in the case of tracking transmission of disease or infection, human-to-human contact is central information of interest. Tracking the locations of humans themselves is therefore desired, but direct tracking is not generally feasible without facial recognition cameras covering every public space imaginable or physical tracking beacons implanted under the skin of every person. It will be appreciated that the following location prediction methods are, most technically, predictions of the locations of mobile devices such as smartphones or wearables (e.g., smartwatches, electronic jewelry, etc.). Studies of human behavior show smartphones and wearables are frequently kept on one's person throughout the day, meaning either in the owner's hand or a pocket or bag (e.g., a purse or handbag) that the human has with him or her at all times or nearly all times. Tracking of a mobile device that connects to Wi-Fi approximates tracking of the person who carries such mobile device. Mobile devices such as smartphones or wearables are preferable tracking targets to laptops, for the simple reason that laptops are less commonly kept on the person at all times throughout a day of activities. Smartphones are commonly carried to bathrooms and sporting events, for example, whereas laptops are not. Laptops may however be used when other more ideal devices are not available, or to improve tracking accuracy with two or more devices belonging to a person that are connected at the same time. For ease of discussion, this disclosure in some instances may refer to "tracking a person" or the like, which may be understood to technically mean "tracking a mobile device" the locations and movements of which correlate or match the locations and movements of a person carrying that mobile device. Similarly, a "person's" location is treated as equivalent and interchangeable with a "device's" location, unless the context specifies otherwise.

Figure 4:
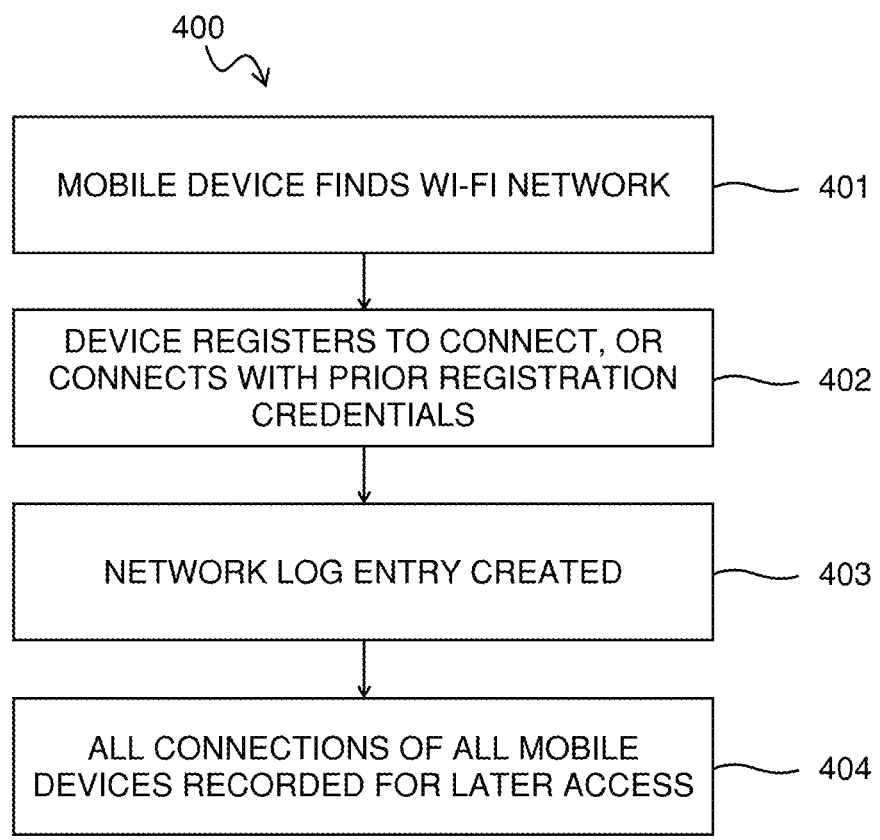
FIG. 4 is a flowchart for logging individuals' AP connections.

The methods P1, P2, and P3 below all rely on access to Wi-Fi network logs. FIG. 4 shows a method 400 for obtaining the Wi-Fi connection information. At step 401 a mobile device finds a discoverable Wi-Fi network. Exemplary methods rely on Wi-Fi networks that require unique connection credentials for each user. Thus at step 402, the user of the mobile device registers to connect with user-specific credentials, or if possessing a prior registration, connects using the pre-existing user credentials. For every connection of every device, a unique network log entry is created at step 403. An exemplary log entry contains at a minimum the identity of the access point (AP) with which the device connects, a unique ID for the connecting mobile device, and date/time (e.g., timestamp) of connection or disconnection from the AP. Every instance of changing from one AP to another AP also creates a distinct log entry at step 403. All connections of all devices are recorded for subsequent access and use. If multiple Wi-Fi networks cover the same locations or the same buildings, the logs for all Wi-Fi networks in such building may be merged together to collectively describe all persons connecting to any Wi-Fi network available.

Wi-Fi log data can be automatically transmitted to one or more analytics servers (computers). For example, network logs can be automatically emailed or securely transmitted through SFTP/SCP protocol on a scheduled basis, i.e., daily at a specific time. Then, the logs are automatically processed to include another day of data into the decision support system. If needed, logs can also be extracted manually by networking personnel if urgently needed to track a specific case outside of the daily schedule.

Figure 5:
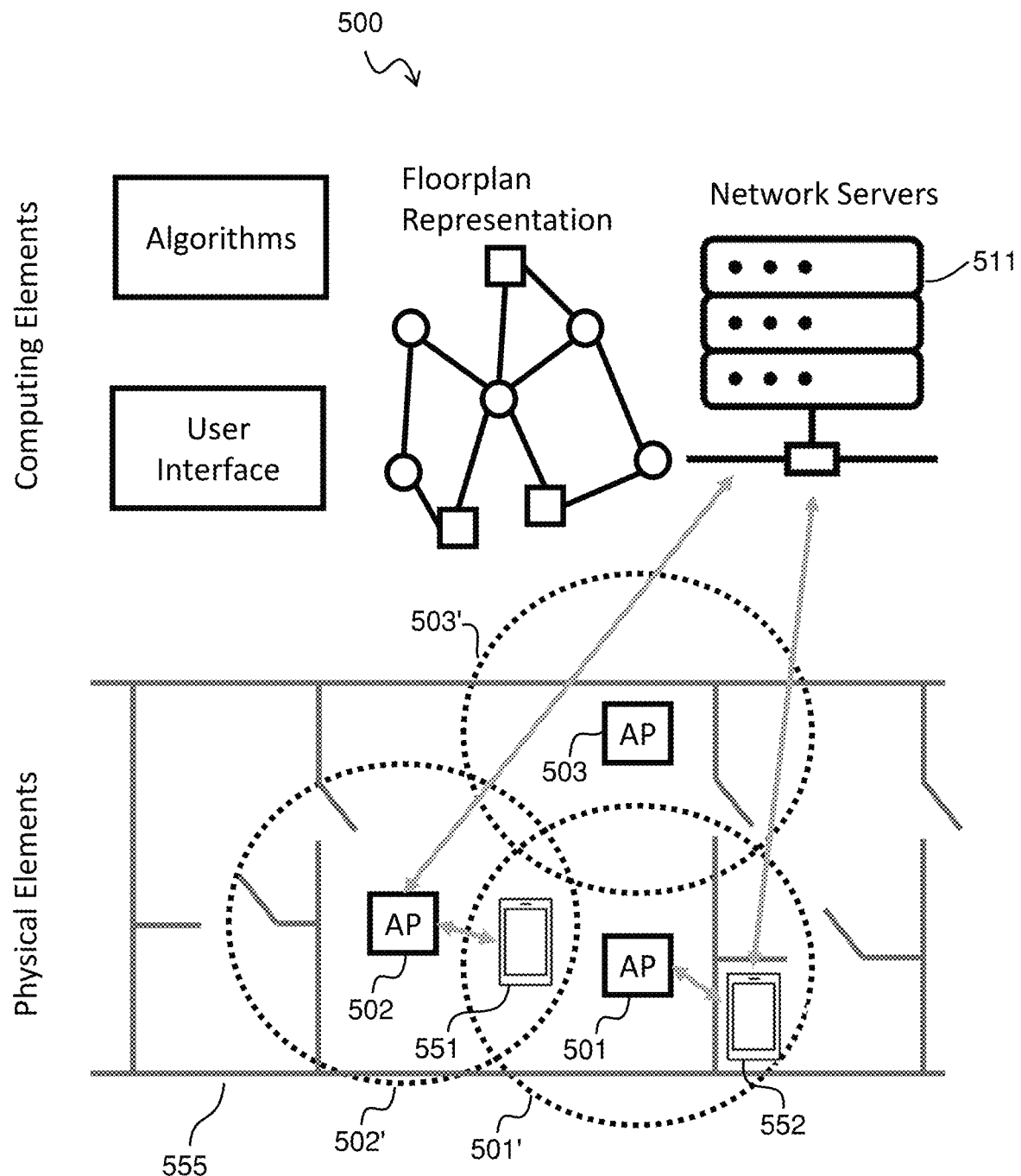
FIG. 5 is a diagram of exemplary system components.

FIG. 5 illustrates the components of an exemplary system 500. The components comprise physical elements including a building 555 of which 5 rooms of a floor are illustrated, access points 501/502/503 and mobile devices 551 and 552. The system 500 further comprises computing elements residing on network servers 511 with floorplan representations, algorithms, and user interfaces.

Location Prediction Approach P1: Wi-Fi Coverage

The P1 approach relies on a Wi-Fi coverage map converted to a list of locations as described above. From the Wi-Fi log data, it is impossible to determine in which of the locations covered by an AP the person is or was present. A single AP may permit connections from a single room, but often an APs signal will reach and therefore permit connection from a plurality of rooms, sometimes even on entirely different floors of a building. Thus, all rooms/locations covered by an AP are considered potential actual rooms/locations of the individual connecting via his or her mobile device. When no additional information is available, the P1 method assigns an equal probability of the person being in any of the covered locations:

$$p(loc_i | AP) = \frac{1}{N_{AP}}$$

where $p(loc_i|AP)$ is the probability of the device/person being at a location i covered by the AP, and $N_{AP}$ is the number of locations covered by the access point AP. When room occupancy information is available, the P1 method may add this additional information to improve the assigned probabilities. Accordingly, the probability of a person being in a room is proportional to the occupancy of the given room, with the assumption that there are more people in larger rooms. The probability assigned to each room i covered by the AP is thus:

$$p(loc_i | AP) = \frac{occ_i}{\sum_{j=1}^{N_{AP}} occ_j}$$

where $occ_i$ is the occupancy of a single room i, $occ_j$ is an occupancy of room j, and $\sum_{j=1}^{N_{AP}} occ_j$ is the total of the combined occupancies of all the rooms covered by the AP.

If no actual occupancy data are available, occupancy per room can be estimated from the area of the room as defined by the International Building Code, e.g. of 2018. (Accordingly, room square area is an additional datum per room/location that may be extracted from floorplans and stored in the location lists during the preparatory stage.) In reality this means the areas of the rooms alone may be used, with probabilities assigned to each room i as follows:

$$p(loc_i | AP) = \frac{area_i}{\sum_{j=1}^{N_{AP}} area_j}$$

where $area_i$ is the square area (e.g., in square meters or square feet) of a single room i, $area_j$ is the square area (e.g., in square meters or square feet) of room j, and $\sum_{j=1}^{N_{AP}} area_j$ is the total of the combined areas of all the rooms covered by the AP.

Any rooms not covered by the AP are assigned a zero probability for the mobile device/person in question for the given time or time duration during which the device/person is connected to the same AP. New probabilities for each room/location are assigned for any subsequent time or time interval where the same device/person disconnects from the first AP and/or connects to another AP different from the first.

As an illustrative example, if a building has 300 rooms identifiable as Room 1 through Room 300, and Person A's mobile device is connected to an AP with coverage in Rooms 37, 39, and 40, each of equal occupancy and/or equal size, then a database spreadsheet may reflected that the probability of Person A being in rooms 37, 39, and 40 are each ⅓ (0.333), and the probability of Person A being in any room other than rooms 37, 39, and 40 is 0.

The determined probabilities for each location for each person connecting to an AP are stored in a database or local storage medium.

Location Prediction Approach P2: Wi-Fi Coverage+Previous Location

The P2 method assigns a probability of a person (or more accurately the person's mobile device) being in a given location not solely based on the Wi-Fi AP with which a connection is made (with or without occupancy or room size data) but also on the person's previous location in time, or more specifically, on the previous AP (and its coverage) to which a person was connected.

Figure 6:
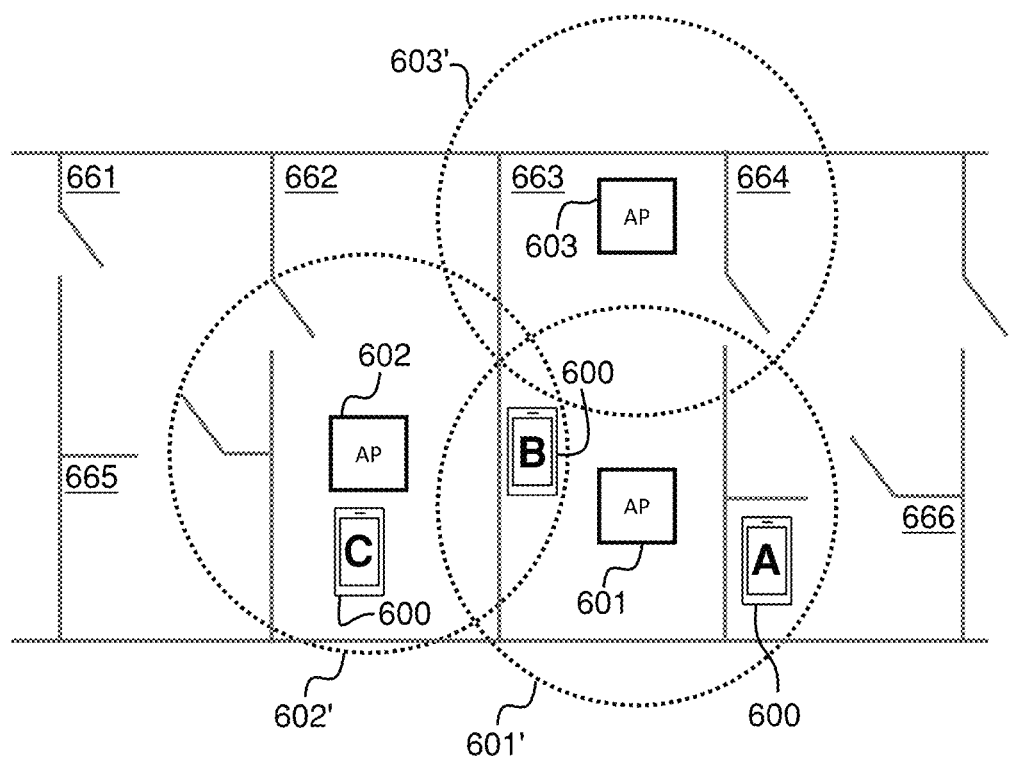
FIG. 6 is an illustration of a switch between access points.

The P2 method is perhaps easiest to introduce with an example. An illustrative scenario is provided by FIG. 6. Three APs 601, 602, and 603 are illustrated each with an indication of that APs signal area 601', 602', and 603' respectively. The APs 601, 602, and 603 collectively provide coverage in six rooms, respectively labeled 661, 662, 663, 664, 665, and 666. Three possible locations of a person/mobile device 600, respectively labeled A, B, and C, are also indicated. Suppose the person is determined or known to be (with the greatest probability of possible locations) at location A and is connected to AP 601. If the person moves to location B, it is unlikely that the person's AP connection will change because the new location is still in range of AP 601. However, if the person moves from location A to location C, a switch to a new AP (e.g., AP 602) will likely occur. Consequently, knowing from network logs that mobile device 600 is first at location A (or at least, that the person was connected to AP 601), then observing from the network logs mobile device 600 next connects to AP 602 after AP 601, it is determinable as unlikely that the person has moved to location B (covered by both the first AP 601 and second AP 602). Rather it is more likely the person has moved to location C.

Therefore, in method P2, the probability assigned to a given location i ($loc_i$) given information about the current AP ($AP_j$) and previous AP ($AP_k$) in the Wi-Fi log is calculated as follows:

$$p(loc_i | AP_j, AP_k) = \begin{cases} \frac{occ_i}{\sum_{j=1}^{N_{AP_j \setminus AP_k}} occ_j} & \text{when } loc_i \in cov_{AP_j} \setminus cov_{AP_k} \\ \frac{1}{\in} & \text{when } loc_i \in cov_{AP_j} \cap cov_{AP_k} \end{cases}$$

where $cov_{AP}$ is the coverage of access point AP and $N_{AP_j \setminus AP_k}$ is the number of locations covered by $AP_j$ and not by $AP_k$. The parameter ∈is is used to allow for a small probability that the switch of AP occurred even if the device is still within the range of the previous AP. In the Example below ∈ was set to 100, but in practice a value for ∈ may be determined through routine optimization. As is the case with the method P1 above, if occupancies are not known, $occ_i$ can be set to one for all locations, or else if room dimensions are known, room square areas may be used instead.

To improve the accuracy of the P2 process in some implementations, locations determined by AP switches may be limited to AP switches which last a predetermined duration of time. For example, a movement of a person from location A to location C to location B in rapid succession (e.g., less than 1 minute, or less than 5 minutes, or less than 10 minutes) may be ignored.

Location Prediction Approach P3: Wi-Fi+Movement

A third exemplary process, so-called P3 approach/method for convenience of discussion, takes into consideration how individuals may move between locations in a building.

Let sloc be a previous known location of the person (for discussion purposes call it a "source location"), and dloc be a new known location (for discussion purposes call it a "destination location"). The nomenclature uses "loc" for a location, "s" for "source", and "d" for "destination". In a large building such as at a university or business, there may be many physical routes to go from sloc to dloc, known in graph theory as simple paths (paths in a node graph with no repeated locations). A building node graph G representing floorplan(s) allows to construct possible paths paths(G, sloc, dloc) between sloc and dloc. Let sp(sloc, dloc) be the shortest path between sloc and dloc and |sp(sloc, dloc)| be its length. When considering two locations at a significant distance from one another in building, there are potentially thousands of possible routes between the locations. In fact, the number of routes may grow exponentially with the length of the path. Various limitations may be implanted to limit the paths considered to a finite limit. In the Examples below, for example, length of paths was limited to $(1+\gamma) \cdot |sp(sloc, dloc)|$, where $\gamma$ is a parameter.

Assuming that all paths between sloc and dloc are equally probable for a person to take, one can count how many times a specific location appears over the entire collection paths(G, sloc, dloc). A probability is assignable to a given location based the ratio of the number of paths containing that location divided by the total number of paths (i.e., both those paths that include the location and those paths that do not include the location).

Note that the assumption of equal probability of a person taking each of the possible paths can be improved upon with actual movement data reflected by the series of APs with which the person connects on route from the source location to the destination location.

When using Wi-Fi access data, a person's location typically cannot be uniquely identified. As already discussed above, a single AP has a reasonable likelihood of allowing connection from multiple rooms, such as adjacent rooms or even rooms on different floors positioned above or below one another. Therefore one needs to consider a set of previous likely locations $$S = \{(sloc_i, p(sloc_i)), i=1,2,\ldots\}$$

where S is the set of possible source locations $sloc_i$ affiliated with a known source AP and $p(sloc_i)$ are probabilities associated with each of the locations $sloc_i$ in the set S, with $\Sigma p(sloc_i) \leq 1$. Similarly, $$D = \{(dloc_j, p(dloc_j)), j=1,2,\ldots\}$$

wherein D is the set of possible destination locations $dloc_j$ affiliated with a known destination AP and $p(dloc_j)$ are probabilities associated with each of the locations $dloc_j$ in the set D, with $\Sigma p(dloc_j) \leq 1$.

Then, paths(G, S, D) is a set of all possible paths including all combinations of locations from S to D. For simplicity, let's assume the independence of sources and destinations for each path, i.e., if a person is at a location A, the person can move with equal probability to any other location B. Then the probability of that path is multiplied by $p(sloc_i)*p(dloc_j)$. When counting locations of all paths, a list of all potentially visited locations is created. The list constitutes potentially visited locations with associated probabilities, and is added to the overall list of predicted locations. Without the independence assumption, one needs to estimate a joint probability $p(dloc_j \wedge dloc_j)$.

The same approach may be taken for a person entering or exiting the building. Every door for entering and exiting the building may be represented as a node in the representative node graph. When a person is observed connecting to his or her first AP in a building (within a specified period of time, e.g. the first connection in a 24 hour window beginning at 12:01 am), there are a limited number of ways in which the person physically reached one of the room nodes having an edge to the connected AP (the destination locations set) starting from any of the building exterior doors permitting entry to the individual in question (the source locations set). The P3 algorithm considers all physically possible routes from outside the building to the locations associated with the first connected AP. Comparably, the very last known AP connection for a predetermined time period (e.g., 24 hours) may be used to produce the source locations set that pairs with a destination locations set that is any of the accessible building exits. After the last AP connection is observed, all possible routes from the location(s) affiliated with the last AP to building exits are calculated.

Exemplary embodiments may use additional reference data or information external to Wi-Fi connection logs to further adjust or improve probabilities assigned to locations for specific individuals. Additional information that may be merged to rule out locations or adjust the probabilities/weights assigned to locations may include but is not limited to: movement patterns from historical data, known office locations, class registration and meeting rosters, class schedules, door smartcard access logs, dedicated sensors such as RFID readers, and electronic health records (showing day/time patients visited specific doctor offices or doctors and at what location(s)).

AP Connection Time and Predicted Location Time

The sections immediately above describe alternative approaches to location prediction. Thus far however the temporal aspects of different persons moving through a building have not yet been fully addressed. Though it's useful to know that two people were in the same room, the risk of "contact" and possible transmission of illness is quite different depending on whether the two people were in the same room at the same time.

To assess whether there was "contact" of one individual (say an individual who is later known to have been infectious while in public) with any other individual, exemplary methods pair each of the first individual's locations (e.g., given as non-zero probabilities as determined above) with a time or time interval (i.e., duration). A convenient frame of reference is the standardized clock time wherever the building with the locations exists. Any two persons that share a non-zero probability for a given location are candidates for a determination of having contacted with one another. However, contact at a given location can be ruled out if the respective times or time intervals for the respective persons at that given location do not overlap to any extent. If they do overlap, then a probability of contact is determined, as explained in greater detail below.

Figure 7:
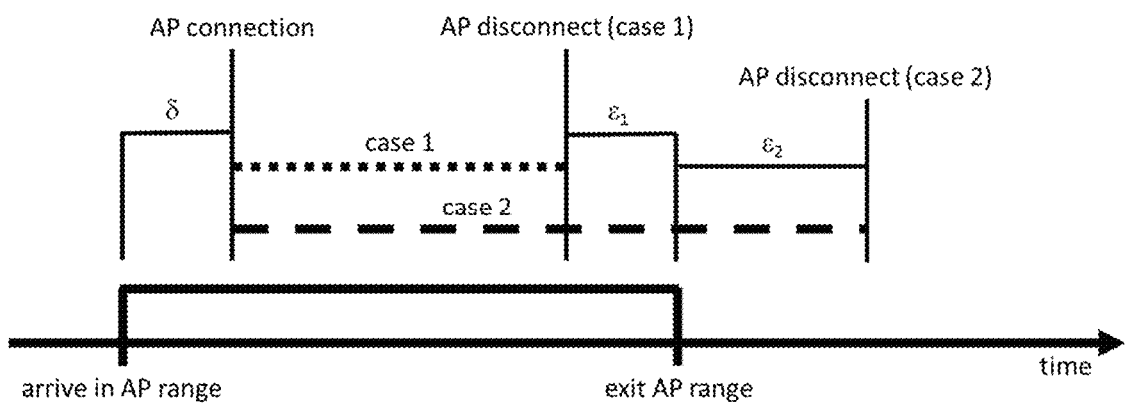
FIG. 7 presents scenarios that illustrate the relationship between location and AP connection and disconnection times.

Before elaborating on the particular of contact scores, it is worth noting an issue that may arise with using AP connection and disconnection times in Wi-Fi network connectivity logs as the basis for measuring time interval at a location. To model the temporal relationship between recorded AP and predicted location the following observations are made: (1) a Wi-Fi device cannot connect to an AP before being in range; (2) the device can connect to an AP at any time while in range; (3) the device can be reported as connected after it is no longer in range (lag in disconnect/switch to new AP); and (3) the device can disconnect from AP anytime while still being in range. Two example scenarios that reflect these realities are illustrated in FIG. 7. In case 1, Wi-Fi connection is established after time $\delta$ from the moment of arriving within range of an AP. The device is disconnected in the interval $\epsilon_1$ before it is moved out of range. In case 2, Wi-Fi connection is established after time $\delta$ from the moment of arriving within range of an AP. The device is disconnected in the interval $\varepsilon_2$ after the device is moved out of range of the AP. The same principle applies when switching between two APs. The device can be already in range of the second access point while still connected to the first one. To simplify these variables, exemplary methods may assume the longest possible connection time when calculating time at location.

Contact Score Calculation

Contact scores provide direct information to public health personnel conducting contact elicitation during a contact tracing process. Contact scores are assigned to individuals that were potentially in contact with an infected person (a person known to be infected). The higher the score, the more at risk an individual is. Intuitively, one can think of the contact score as an expected time of contact, but the actual formula is more complex. Public health personnel can rank individuals by the score to prioritize follow up.

Let $p_I(loc_i)$ be probability of the infected individual I being at a location $loc_i$ at a given time. Similarly, let $p_C(loc_i)$ be probability of potential contact individual C being at the location $loc_i$ at the same time. Assuming that $p_I(loc_i)$ and $p_C(loc_i)$ are independent, i.e., there is no relation between movements of the two individuals, the probability of both being at the location $loc_i$ is $p_I(loc_i) \cdot p_C(loc_i)$. Let $t(loc_i)$ be predicted time interval in which both individuals were at $loc_i$. $t(loc_i)$ can be calculated by intersecting time intervals during which individuals I and C were at the location i. The contact score CS between infected person I and potential contact individual C may be defined as:

$$CS(I, C) = \sum_i \omega_i \cdot p_I(loc_i) \cdot p_C(loc_i) \cdot t(loc_i)$$

where $\omega_i$ is a parameter characterizing type of location in relation to the risk of the disease transmission. Locations such as elevators or small offices have high values of $\omega$, while large areas such as lecture halls have comparatively lower co. For simplicity, in the presented Examples below, all values of $\omega$ were set to one. However, based on the disease spread characteristics one can estimate their values for different locations, and calibrate the value in real-time as the system is being deployed.

The processor(s) of servers (or other types of computers) may, after the contact scores are produced and compiled, initiate one or more signals to transmit identification of the respective persons whose contact scores are above a predetermined threshold. This may be performed in response to a user search query with inputs such as the identity of a target person (e.g., an infected individual or person of interest) and a time period (e.g., a one or two week window). The output resulting from such a query may be a list of locations where the target person visited during the time period and a list of contacts at those locations above a predetermined contact score threshold, for example. The signals initiated by the one or more processors may cause a list of the respective persons whose contact scores are above the predetermined threshold to be sent to a contact tracing coordinator. In addition or as an alternative, the signals initiated by the one or more processors may cause push notifications to be sent to the respective first mobile devices of the respective persons to alert of an exposure risk with the target person.

Some embodiments of the present invention may be a system, a device, a method, and/or a computer program product. A system, device, or computer program product may include a computer readable storage medium (or media) having computer readable program instructions thereon for causing a processor to carry out aspects of the present invention, e.g., processes or parts of processes or a combination of processes described herein.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Processes described herein, or steps thereof, may be embodied in computer readable program instructions which may be paired with or downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, Python, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions and in various combinations.

These computer readable program instructions may be provided to one or more processors of one or more general purpose computers, special purpose computers, or other programmable data processing apparatuses to produce a machine or system, such that the instructions, which execute via the processor(s) of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the invention has been described herein in connection with exemplary embodiments and features, one skilled in the art will recognize that the invention is not limited by the disclosure and that various changes and modifications may be made without departing from the scope of the invention as defined by the appended claims.

EXAMPLES

Example 1: Location Prediction

This Example studies the effectiveness of movement tracking methods described above by comparing predictive approaches against predetermined participant movement paths. The presented Wi-Fi data modeling was implemented using Python programming language and utilized Pandas library for general data processing, Scikit-Learn for machine learning and model evaluation, and NetworkX for graph modeling and analysis.

Ideally, one would like to construct a model that precisely and correctly predicts the locations of an individual over time. Below, location-recall (L-R) specifies the proportion of locations at which a person was really present and that were correctly identified. Location confidence (L-C) is defined as the proportion of correctly identified locations to all locations returned by the model. The terms location-recall and location-confidence are specifically used to avoid confusion with similar standard metrics used in binary classification. L-C is used because metrics such as precision used in binary classification are not applicable here. L-R and L-C are used to describe the location prediction accuracy of each model.

Let TP be a number of true positives that is a set of correctly predicted locations for a person to be at; FP be number of false positives that are locations at which the person was not present, but that were identified by the model; TN be number of true negatives that is a set of locations correctly predicted for the person not to be at; and FN be number of false negatives that is a set of locations in which the person was present, but that were missed by the model. |predictions| indicates the number of predicted locations in which a person can be (when methods are unable to pinpoint one specific location).

$$location\check{\ }recall = \frac{TP}{TP+FN}$$

$$location\check{\ }confidence = \frac{TP}{|predictions|}$$

$$confidence\ gain = \frac{confidence}{no\ information}$$

The last metric, confidence gain (CG), shows an improvement of confidence over a situation in which a person can be in any location in a building, which is $$\frac{1}{|locations|}$$

with |locations| being the total number of rooms in the building. In the presented work there are 450 locations in the building. For example, CG=10 indicates that the prediction is 10 times better than saying that a person is somewhere in the building without any greater specificity. The idea of location-confidence is somewhat similar to one used in the rough set theory presented in Pawlak, Zdzislaw (1982). "Rough sets". International Journal of Parallel Programming. 11 (5): 341356. It is also used in machine learning software such as AQ21 that can output more than one predicted class in output (non-definitive answer) (see (Wojtusiak, J., Michalski, R. S., Kaufman, K. and Pietrzykowski, J., "The AQ21 Natural Induction Program for Pattern Discovery: Initial Version and its Novel Features," Proceedings of The 18th IEEE International Conference on Tools with Artificial Intelligence, Washington D.C., Nov. 13-15, 2006.).

For this Example, manual extraction of the floorplan depicted in FIG. 3A for one building was completed. For organizations such as universities, it is not unusual that each large building has a facility manager that can be responsible for completing the work. With proper coordination, the process can be completed in a relatively short time for entire campuses. Moreover, the extraction does not require any specific qualifications beyond the ability to read floorplans and the use of spreadsheet applications in view of the explanations of this disclosure.

The extracted data were in the form of a flat table e.g. typed in Excel or a similar application. The table comprised four columns: location1, location2, passage-type, and locked. Essentially, at a most basic level, to model a floorplan requires minimally modeling openings that permit passage between locations. In this case, locations can be rooms, corridors or open areas as shown on the floorplan. For purposes of discussion "room" is sometimes used generically in this disclosure to refer to any multidimensional space a person may spend time. In the undirected graph used, the order of location1 and location2 is irrelevant. Passage-type indicates door, double door, or hallway. Locked indicates if the doors are typically locked. Modeling which doors are locked allows for modeling access to different areas, and can be further complemented by information about accessibility by specific individuals, if available. Connections between floors are modeled through staircases and elevators that link corridors of different floors. The graph can then be verified automatically and by another person (i.e., by searching for locations disjoint from others). There are published works on automated graph extraction from floorplans. For example, Schmitt et al. presented an approach to routing graph generation from 2-dimensional floorplans (S. Schmitt et al., "Fast routing graph extraction from floor plans," 2017 International Conference on Indoor Positioning and Indoor Navigation (IPIN), Sapporo, 2017, pp. 1-8, doi: 10.1109/IPIN.2017.8115868.). Such methods may be applied by those of skill in the art.

In this Example, the mapped building is located at George Mason University's Fairfax campus. Floorplans with Wi-Fi locations were readily available in the university's Information Technology Office and transcribed into a spreadsheet. The single building was represented by a graph with 450 nodes with 392 nodes representing rooms, 53 nodes representing passages and hallways, 3 staircases, 2 elevators, and 667 edges connecting the nodes. 98 Wi-Fi access points in the building were represented as AP-type nodes which were linked to location nodes within their coverage using edges, which additionally carry information about estimated RSSI in the building. Because floorplans are "flat", but Wi-Fi signal is 3-dimensional spanning across floors, some accounting was made when converting the floorplans into a node graph. In the simplified approach used, the adjacent floor coverage was modeled with signal strength reduced by 25 dB. This approach allowed for turning 2-dimensional floorplans into a 3-dimensional Wi-Fi coverage model.

Based on the distance to an access point, theoretical RSSI can be calculated given the transmit power of the access point. A majority of Wi-Fi access points in the building were at frequency of 5,000 MHz, and some of them were 2,400 Mhz.

Coverage of any given AP may be determined theoretically and/or empirically. A theoretical coverage map was used in this Example. While empirical results are superior to theoretical coverage maps, empirical coverage data collection is a more time-consuming process that is not necessarily feasible in all implementations, especially those that aim for fast deployment of tracking systems, e.g., in answer to a public health crisis or outbreak.

Wi-Fi data used for technology-based contact tracing may be collected by enterprise-level Wi-Fi networks. The Wi-Fi data used in this Example was generated using SNMP (Simple Network Management Protocol) traps. Each time a mobile device (e.g., smartphone or laptop) connected to a network, a record in a network log was created. Since the connection required users to login using their credentials (manually if connecting for the first time, or automatically with saved credentials for repeat users), it is possible to identify individuals connected at the same time. There is wide use of Wi-Fi networks in environments such as university campuses.

The data used here in this Example indicates that within a 31-day period in October/November 2020, the Wi-Fi network at the university campus was accessed by about 21,000 unique users. Interviews of selected students indicated that all of them use the campus Wi-Fi network. While this information is anecdotal and does not provide evidence of the Wi-Fi use, it is consistent with the high number of Wi-Fi users. One proper way of estimating Wi-Fi usage would be to count people entering a building in a given period and compare that data to the Wi-Fi usage.

The Wi-Fi log data are relatively large. One month of data in February 2021 contains about 870,000 rows, and that number corresponds with a time period when the university was only partially open during COVID-19 pandemic. During full academic operations (in a pre-COVID time for instance), the data may exceed 2 million rows every month.

The location prediction methods N1, N2, P1, P2 and P3 described above were applied to scenario data collected from 12 study participants. Data for scenarios with no corresponding Wi-Fi logs were removed. 101 unique scenarios were developed to account for different types of movements within a building. The scenarios were distributed to 12 study participants who manually recorded exact times they were in specific locations, with a total number of 158 performed scenarios (some scenarios were completed by more than one participant). The participants had their personal mobile devices on their persons while moving through the scenarios, and their mobile devices were on and connected to the Wi-Fi network. In preparation for the study, the participants received temporary access to typically locked parts of the building (their keycards were programmed for access). The times and locations manually recorded by the participants as they walked the routes prescribed by their scenarios were later transcribed and converted into a data file.

Three of the scenarios were not performed by any participants because of issues with access to certain parts of the building. This is because their keycards were not correctly programmed to include all locations before the study began. In some cases, participants indicated that they waited for a certain time in front of a door they could not unlock. These were marked in data as variants of the original scenarios. In total, 158 scenarios were performed, as previously mentioned. The manually recorded locations and times recorded by participants were merged with the Wi-Fi log data that resulted from the participants' mobile device connections with the Wi-Fi network. After merging, it was found that 120 out of the 158 (76%) completed scenarios had corresponding Wi-Fi data. Further investigation of the reasons for missing scenarios indicated problems with phones not connecting during the entire study period for one participant, and during one day for another participant. For other participants, some of the missing scenarios are the ones that were performed outside the building (to test external Wi-Fi coverage). While the missing scenario data are invalid for the purpose of this Example, they were used to calculate recall (sensitivity) of the Wi-Fi tracking, indicating that some people may be missing in the access data. Another typical problem with Wi-Fi connection occurs after a password reset in the enterprise system which needs to be updated to connect to Wi-Fi.

The average length of completed scenarios was 32.7+/−18.8 minutes and included 11.55+/−3.42 distinct locations. On average, participants stayed in a location for 86.79 sec (144.5 sec when excluding corridors and hallways). The summary of the scenario data is available in Table 1. This duration is significantly shorter when compared to patterns of real use of the building. As mentioned previously, the expected range of AP signal was not empirically tested in the building but assigned coverage based on theoretical prediction. The resulting data used in this Example shows an average of 3.61±2.01 rooms (this includes corridors, restrooms, staircases, and elevators) per access point at RSSI −50, 14.87±6.53 rooms per access point at RSSI −70, 73.98±26.31 rooms per access point at RSSI −85. Consequently, each room/location is covered by an average an 0.72±0.71 APs at RSSI −50, 2.95±1.55 APs at RSSI −70, 14.69±4.56 APs at RSSI −85.

The scenarios were designed to emphasize movement of individuals. In real data one can expect people to stay at individual locations for much longer, e.g., when attending a lecture or a meeting, or working at a desk or table. Consequently, data from other implementations of exemplary embodiments are expected to be easier to analyze. The discrepancy between connection times for the normal building use and the scenarios was partially addressed in the simulated-contact data described later in this Example and used to test predicted contacts.

TABLE 1

Summary of the collected scenario data.

| | All scenario locations | | | | Rooms only | | | |
| --- | --- | --- | --- | --- | --- | --- | --- | --- |
| | Mean | Std | min | max | Mean | Std | min | max |
| # locations | 19.85 | 7.21 | 7 | 48 | 2.71 | 2.3 | 0 | 10 |
| # distinct locations | 11.55 | 3.42 | 5 | 26 | 2.07 | 1.31 | 0 | 5 |
| scenario duration (sec) | 1962.28 | 1121.2 | 420 | 6360 | 653.33 | 539 | 0 | 2630 |
| Time at location (sec) | 86.79 | 101.50 | 0.0 | 1800 | 144.5 | 124.8 | 0 | 935 |
| # floors in scenario | 2.45 | 1.4 | 0 | 5 | — | — | — | — |
| # Access Points | 3.19 | 1.58 | 1 | 9 | — | — | — | — |
| # distinct Access Points | 2.89 | 1.21 | 1 | 6 | — | — | — | — |
| AP connect time (sec) | 1250.96 | 659.65 | 302 | 3336 | 610.63 | 538.85 | 0 | 2630 |
| # locations of RSSI: −50 | 2.29 | 1.92 | 0 | 10 | 0.61 | 1.1 | 0 | 6 |
| # locations of RSSI: −70 | 5.13 | 3.69 | 0 | 20 | 1.38 | 1.95 | 0 | 12 |
| # locations of RSSI: −85 | 8.85 | 4.97 | 0 | 22 | 2.6 | 2.63 | 0 | 13 |

In Table 1, "distinct" means locations and APs were not double counted when a person moves in and out. The "time at location (sec)" row is the average of the times of all 12 participants for all locations each participant visited.

As mentioned above, the manually recorded data from the enacted scenarios and Wi-Fi data retrieved during the scenarios were merged to allow for comparing real locations (as manually recorded by participants) and predicted locations (using the P1, P2, and P2 methods and Wi-Fi data). The two datasets were merged by a participant ID and aligned by time. Since there is no one-to-one correspondence between scenario steps and the Wi-Fi dataset, additional rows of the data were created.

Not surprisingly, the P1, P2, and P3 methods that predict locations yielded better performance than the N1 and N2 approaches discussed in the Background section. Note that the sample size for locations in which individuals stayed for more than 10 minutes is small. The methods have relatively good recall. The gain (over no room information) was more than 100-fold. The best results were obtained from method P3 that combined the movement of people through the building with the P1 approach to predicting when people are connected to a Wi-Fi AP. When only movement is modeled, method P3-Move also shows accurate results.

TABLE 2

Summary of experimental results comparing approaches to location prediction on scenario data. Results are reported in terms of recall, confidence and confidence gain. P1 −50, P1 −70 and P1 −85 correspond to method P1 with minimum RSSI as indicated.

| Method | All data, N = 1271 | | | 5+ minutes, N = 100 | | | 10+ minutes, N = 6 | | |
|---|---|---|---|---|---|---|---|---|---|
| | LR | LC | CG | LR | LC | CG | LR | LC | CG |
| N1 | 3.462% | 100% | 450 | 11.0% | 100% | 450 | 16.67% | 100.0% | 450 |
| N2 | 89.77% | 0.189% | 1 | 99% | 0.19% | 1 | 100% | 0.19% | 1 |
| P1 −50 | 10.54% | 40.99% | 216.8 | 20.2% | 35.6% | 188 | 16.67% | 44.048% | 233 |
| P1 −70 | 28.40% | 8.86% | 46.87 | 48.0% | 7.39% | 39 | 50.0% | 10.05% | 53.18 |
| P1 −85 | 40.83% | 2.89% | 12.47 | 59.0% | 2.62% | 1.38 | 50.0% | 3.34% | 17.65 |
| P3 | 89.77% | 24.02% | 127.08 | 79.17% | 17.16% | 90 | 85.71% | 17.65% | 93.34 |

Example 2: Contact Prediction

This Example relies on a dataset which used as its basis the same empirical data collected using 12 participants walking predetermined movement path scenarios, as described in Example 1 above. However, Because the data was collected at the peak of COVID-19 pandemic, it was not possible to have participants actually be in contact with each other when performing the scenarios. Instead, the 12 participants conducted the scenarios independently and at different times. After the data was collected, the scenarios respective datasets were artificially aligned in time to simulate the participants contacting one another as their movement paths through the building overlapped with one another in space and time. Such data manipulation does not affect evaluation of the methods—times of real recorded locations and Wi-Fi connections are shifted together.

The "one-day" synthetic data simulates a pre-defined number of individuals accessing a building at different times within an 8-hour period. The data were created by sampling with replacement, randomly positioning in time, and stretching participant-scenarios. Each randomly selected scenario was assigned a random start time within the 8-hour period. If the scenario overlapped in time with another copy of itself, it was discarded, and another scenario was selected. This process was repeated until the desired number of synthetic individuals was created. First, the number of simulated individuals was based on Wi-Fi access logs for all people in the building between September 2020 and January 2021 (Experiment 1). Then, 100, 200, 500 and 1000 synthetic individuals were considered to check contact patterns at varying numbers of individuals (Experiment 2).

Figure 8:
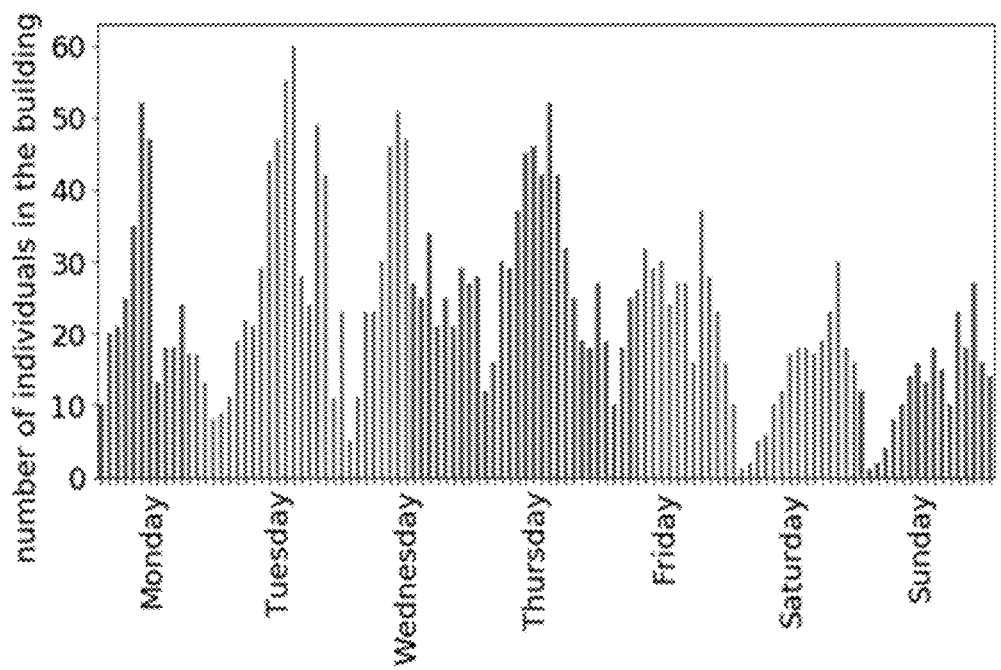
FIG. 8 is sample data showing hourly distribution of individuals in a university building for one week.

While the "one-day" synthetic data simulates the desired number of synthetic individuals, it does not reflect the distribution patterns in the building at different hour of a day. To keep the synthetic data consistent with the distribution pattern, the synthetic individuals in the building following hourly distributions patterns are also generated. FIG. 8 shows the total number of individuals each hour between 8 am to 11 pm during an average week. During the semester, each week, the total number of individuals accessing the building varies. Around the seventh to the ninth week of the semester, the total number of individuals is about 4000/ week, and at the beginning or end of the semester or winter break, it is significantly less. The distributions shown in FIG. 8 are used to generate the synthetic data patterns at a specified time period.

Besides shifting recorded locations and Wi-Fi connections, times at specified locations were also stretched. The 12 participants' in-building time in the preformed scenarios were on average about 15 minutes. However, in a real scenario, the time of stay varies between several minutes to hours. A list of locations, most of which are classrooms or study lounges, were selected for time stretching. If a participant was in one of the locations listed, a randomly stretched time is added to both the locations and Wi-Fi connections (Experiments 3 and 4).

Contact prediction can be defined as a binary classification problem. The results are reported in terms of standard metrics: area under Receiver-Operator Curve (ROC) (AUC), accuracy, recall, and precision. Extensive evaluation of methods for contact prediction were conducted. When simulating one day of data in a building, the number of people entering the building was changed between 100 and 1000. These numbers are consistent with the real numbers of people who accessed a sample building on a university campus daily in October 2020: about 400±30 during weekdays and about 150±50 on weekends. To calculate average performance of the method, the simulation assumed that one person is infected, and all contacts are predicted to calculate accuracy metrics. This is then repeated for all people in the data, assuming that every person is infected one-by-one, one at a time. All experiments were performed separately for each day of the week. All experiments were repeated 10 times, resulting in a total of 700 simulated datasets. All discussed prediction methods were applied and tested on all of the simulated datasets. The summary of results is presented in Table 3.

TABLE 3

Summary of experimental results on the "one day" simulated data.

| | #cont. | Meth. | AUC | Accuracy | Recall | Precision |
|---|---|---|---|---|---|---|
| Non-stretched, real distribution | 1.46 ± 0.79 max: 8 | n1 | 0.58 ± 0.17 | 0.19 ± 0.38 | 0.16 ± 0.33 | 0.19 ± 0.38 |
| | | n2 | 0.90 ± 0.19 | 0.50 ± 0.35 | 0.80 ± 0.37 | 0.50 ± 0.35 |
| | | p1 | 0.76 ± 0.23 | 0.41 ± 0.43 | 0.46 ± 0.46 | 0.41 ± 0.43 |
| | | p1 −50 | 0.60 ± 0.18 | 0.23 ± 0.40 | 0.20 ± 0.37 | 0.23 ± 0.40 |
| | | p1 −70 | 0.69 ± 0.22 | 0.33 ± 0.43 | 0.34 ± 0.43 | 0.33 ± 0.43 |

TABLE 3-continued

Summary of experimental results on the "one day" simulated data.

| | #cont. | Meth. | AUC | Accuracy | Recall | Precision |
|---|---|---|---|---|---|---|
| | | p2 | 0.76 ± 0.23 | 0.41 ± 0.43 | 0.46 ± 0.46 | 0.41 ± 0.43 |
| | | p3 | 0.86 ± 0.21 | 0.50 ± 0.39 | 0.67 ± 0.43 | 0.50 ± 0.39 |
| Stretched, real distribution | 1.51 ± 0.86 max: 7 | n1 | 0.59 ± 0.17 | 0.20 ± 0.38 | 0.17 ± 0.34 | 0.20 ± 0.38 |
| | | n2 | 0.88 ± 0.19 | 0.30 ± 0.27 | 0.77 ± 0.39 | 0.30 ± 0.27 |
| | | p1 | 0.74 ± 0.23 | 0.29 ± 0.36 | 0.44 ± 0.45 | 0.29 ± 0.36 |
| | | p1 −50 | 0.60 ± 0.18 | 0.21 ± 0.37 | 0.21 ± 0.37 | 0.21 ± 0.37 |
| | | p1 −70 | 0.69 ± 0.22 | 0.28 ± 0.38 | 0.34 ± 0.43 | 0.28 ± 0.38 |
| | | p2 | 0.74 ± 0.23 | 0.29 ± 0.36 | 0.44 ± 0.45 | 0.29 ± 0.36 |
| | | p3 | 0.83 ± 0.21 | 0.34 ± 0.33 | 0.62 ± 0.44 | 0.34 ± 0.33 |
| Non-stretched, 100-1000 indiv. | 1.80 ± 1.20 max: 12 | n1 | 0.58 ± 0.15 | 0.21 ± 0.39 | 0.15 ± 0.31 | 0.21 ± 0.39 |
| | | n2 | 0.88 ± 0.18 | 0.42 ± 0.32 | 0.77 ± 0.37 | 0.42 ± 0.32 |
| | | p1 | 0.75 ± 0.22 | 0.38 ± 0.40 | 0.44 ± 0.44 | 0.38 ± 0.40 |
| | | p1 −50 | 0.60 ± 0.17 | 0.24 ± 0.39 | 0.20 ± 0.34 | 0.24 ± 0.39 |
| | | p1 −70 | 0.69 ± 0.21 | 0.32 ± 0.40 | 0.33 ± 0.41 | 0.32 ± 0.40 |
| | | p2 | 0.75 ± 0.22 | 0.38 ± 0.40 | 0.44 ± 0.44 | 0.38 ± 0.40 |
| | | p3 | 0.86 ± 0.20 | 0.42 ± 0.34 | 0.67 ± 0.41 | 0.42 ± 0.34 |
| Stretched, 100-1000 indiv. | 1.62 ± 1.00 max: 10 | n1 | 0.59 ± 0.17 | 0.20 ± 0.38 | 0.17 ± 0.34 | 0.20 ± 0.38 |
| | | n2 | 0.88 ± 0.19 | 0.29 ± 0.27 | 0.76 ± 0.39 | 0.29 ± 0.27 |
| | | p1 | 0.74 ± 0.23 | 0.29 ± 0.35 | 0.44 ± 0.45 | 0.29 ± 0.35 |
| | | p1 −50 | 0.60 ± 0.18 | 0.21 ± 0.37 | 0.20 ± 0.36 | 0.21 ± 0.37 |
| | | p1 −70 | 0.69 ± 0.22 | 0.28 ± 0.38 | 0.34 ± 0.42 | 0.28 ± 0.38 |
| | | p2 | 0.74 ± 0.23 | 0.29 ± 0.35 | 0.44 ± 0.45 | 0.29 ± 0.35 |
| | | p3 | 0.83 ± 0.21 | 0.33 ± 0.32 | 0.61 ± 0.43 | 0.33 ± 0.32 |

Figure 9:
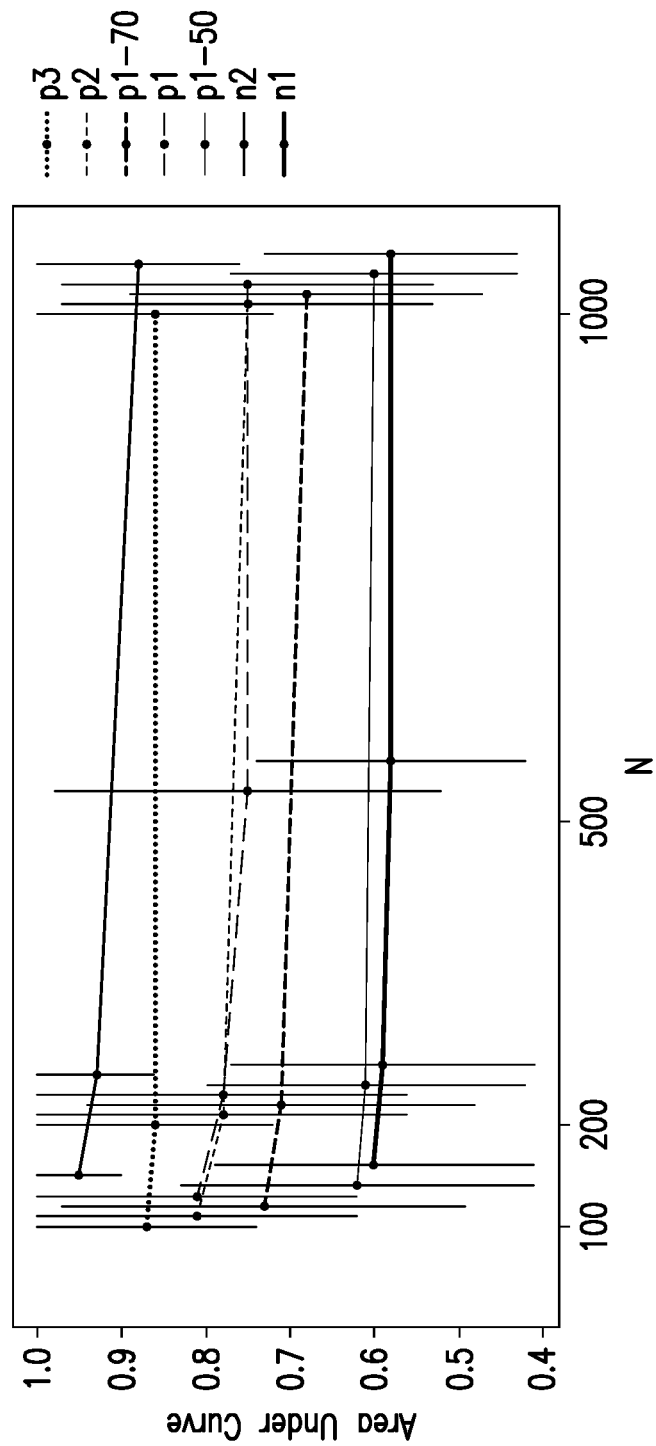
FIG. 9 is area under ROC (AUC) of models with varying number of people in a building over 8-hour period.

The results confirm that the P3 method that models locations and movements achieves better performance than other location prediction methods. However, the overall AUC appears lower than that of the N2 method. Detailed analysis of results indicated that none of the prediction location methods are able to identify all contacts (and ROC line does not reach value 1), thus lower AUC. FIG. 9 shows the relationship between number of people in the building and AUC of models. The AUC is not affected by the number of people, yet the average number of contacts grows from 4 contacts with 100 people in the building to 12 contacts with 1000 people in the building (pairwise contacts).

The results of this Example confirm that Wi-Fi data is usable to support contact tracing. The investigated approaches to location prediction can be used to complement data collected during public health case interviews, as part of the contact tracing during a communicable disease outbreak or in the time of a pandemic such as with COVID-19.

What is claimed is:

1. A method of tracing contact of a target person with other people, comprising
   extracting Wi-Fi access point (AP) information for a plurality of mobile devices, each of the plurality of mobile devices being associated with a different individual of a plurality of people, the Wi-Fi access point information containing, for each mobile device, a list of one or more APs used for connecting to a network, one or more connection times of when the respective mobile device connected to each of the one or more APs, and one or more disconnection times of when the respective mobile device disconnected from each of the one or more APs;
   for each AP connection of each mobile device, assigning a non-zero probability to any locations from which signal of the AP permits a connection and a zero probability to remaining locations;
   for each of one or more times or time intervals for each respective person of one or more of the people, determining a contact score between a first mobile device of the respective person and a second mobile device of a target person using the assigned probability for a first location for the first mobile device and the assigned probability for the first location for the second mobile device.

2. The method of claim 1, further comprising initiating one or more signals to transmit identification of the respective persons whose contact scores are above a predetermined threshold.

3. The method of claim 2, wherein the one or more signals cause push notifications to be sent to the respective first mobile devices of the respective persons to alert of an exposure risk with the target person.

4. The method of claim 2, wherein the one or more signals cause a list of the respective persons whose contact scores are above the predetermined threshold to be sent to a contact tracing coordinator.

5. The method of claim 1, wherein the non-zero probabilities assigned to the locations from which signal of the AP permits a connection are each an equal probability, and the sum of the non-zero probabilities is 1.

6. The method of claim 1, wherein the non-zero probabilities assigned to the locations from which signal of the AP permits a connection are each proportional to either a maximum occupancy or a square area of the respective location, and the sum of the non-zero probabilities is 1.

7. The method of claim 1, wherein the non-zero probabilities assigned to the locations from which signal of the AP permits a connection are based in part on a record of a prior AP to which the respective mobile device connected.

8. The method of claim 1,
   wherein the non-zero probabilities assigned to the locations from which signal of the AP permits a connection are based in part on a probability of each respective location being included in a movement path between a source location and a destination location, and
   wherein
      the source location corresponds with one AP with which the mobile device connected and the destination location corresponds with a second AP with which the mobile device connected after disconnecting with the one AP, or the source location is a building entrance and the destination location is an AP with which the respective mobile device connected, or wherein the source location is an AP with which the respective mobile device connected and the destination location is a building exit.

9. A system for tracing contact of a target person with other people, comprising a computer readable storage medium with non-transitory computer-readable program instructions;

one or more processors which, upon execution of the computer-readable program instructions, are caused to perform extracting Wi-Fi access point (AP) information for a plurality of mobile devices, each of the plurality of mobile devices being associated with a different individual of a plurality of people, the Wi-Fi access point information containing, for each mobile device, a list of one or more APs used for connecting to a network, one or more connection times of when the respective mobile device connected to each of the one or more APs, and one or more disconnection times of when the respective mobile device disconnected from each of the one or more APs, for each AP connection of each mobile device, assigning a non-zero probability to any locations from which signal of the AP permits a connection and a zero probability to remaining locations, for each of one or more times or time intervals for each respective person of one or more of the people, determining a contact score between a first mobile device of the respective person and a second mobile device of a target person using the assigned probability for a first location for the first mobile device and the assigned probability for the first location for the second mobile device.

10. The system of claim 9, further comprising one or more user interfaces for accessing the contact scores or lists generated from the contact scores.

11. The system of claim 9, wherein processors are further caused to perform initiating one or more signals to transmit identification of the respective persons whose contact scores are above a predetermined threshold.

12. The system of claim 11, wherein the one or more signals cause push notifications to be sent to the respective first mobile devices of the respective persons to alert of an exposure risk with the target person.

13. The system of claim 11, wherein the one or more signals cause a list of the respective persons whose contact scores are above the predetermined threshold to be sent to a contact tracing coordinator.

14. The system of claim 9, wherein the non-zero probabilities assigned to the locations from which signal of the AP permits a connection are each an equal probability, and the sum of the non-zero probabilities is 1.

15. The system of claim 9, wherein the non-zero probabilities assigned to the locations from which signal of the AP permits a connection are each proportional to either a maximum occupancy or a square area of the respective location, and the sum of the non-zero probabilities is 1.

16. The system of claim 9, wherein the non-zero probabilities assigned to the locations from which signal of the AP permits a connection are based in part on a record of a prior AP to which the respective mobile device connected.

17. The system of claim 9, wherein the non-zero probabilities assigned to the locations from which signal of the AP permits a connection are based in part on a probability of each respective location being included in a movement path between a source location and a destination location, and wherein the source location corresponds with one AP with which the mobile device connected and the destination location corresponds with a second AP with which the mobile device connected after disconnecting with the one AP, or the source location is a building entrance and the destination location is an AP with which the respective mobile device connected, or wherein the source location is an AP with which the respective mobile device connected and the destination location is a building exit.

18. A non-transitory computer program product comprising instructions which, when executed by one or more processors, cause the one or more processors to perform extracting Wi-Fi access point (AP) information for a plurality of mobile devices, each of the plurality of mobile devices being associated with a different individual of a plurality of people, the Wi-Fi access point information containing, for each mobile device, a list of one or more APs used for connecting to a network, one or more connection times of when the respective mobile device connected to each of the one or more APs, and one or more disconnection times of when the respective mobile device disconnected from each of the one or more APs, for each AP connection of each mobile device, assigning a non-zero probability to any locations from which signal of the AP permits a connection and a zero probability to remaining locations, for each of one or more times or time intervals for each respective person of one or more of the people, determining a contact score between a first mobile device of the respective person and a second mobile device of a target person using the assigned probability for a first location for the first mobile device and the assigned probability for the first location for the second mobile device.

* * * * *